United States Patent
Stössel et al.

(10) Patent No.: US 8,304,542 B2
(45) Date of Patent: Nov. 6, 2012

(54) METAL COMPLEXES AND THEIR USE AS THE EMITTING CONSTITUENT IN ELECTRONIC COMPONENTS, IN PARTICULAR IN ELECTROLUMINESCENT DISPLAY DEVICES

(75) Inventors: Philipp Stössel, Frankfurt am Main (DE); Rocco Fortte, Frankfurt (DE); Amir Parham, Frankfurt (DE); Horst Vestweber, Gilersberg-Winterscheid (DE); Holger Heil, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 636 days.

(21) Appl. No.: 11/721,253

(22) PCT Filed: Dec. 6, 2005

(86) PCT No.: PCT/EP2005/013044
§ 371 (c)(1),
(2), (4) Date: Aug. 11, 2009

(87) PCT Pub. No.: WO2006/061182
PCT Pub. Date: Jun. 15, 2006

(65) Prior Publication Data
US 2009/0292080 A1 Nov. 26, 2009

(30) Foreign Application Priority Data
Dec. 9, 2004 (EP) .................................... 04029182

(51) Int. Cl.
*C07F 15/00* (2006.01)
*C08F 8/00* (2006.01)

(52) U.S. Cl. ............................................. 546/4; 525/370
(58) Field of Classification Search ....... 546/4; 525/370
See application file for complete search history.

(56) References Cited

U.S. PATENT DOCUMENTS

| 2004/0138455 A1 | 7/2004 | Stossel et al. |
| 2005/0176958 A1 | 8/2005 | Stossel et al. |

FOREIGN PATENT DOCUMENTS

| EP | 0120673 | A2 | 10/1984 |
| EP | 0525739 | A1 | 2/1993 |
| EP | 1211257 | A2 | 6/2002 |
| EP | 1348711 | A1 | 10/2003 |
| EP | 1400514 | A1 | 3/2004 |
| KR | 2010111085 | A * | 10/2010 |
| TW | I-242393 | | 10/2005 |
| WO | WO-02/068435 | A1 | 9/2002 |
| WO | WO-03/040160 | A1 | 5/2003 |
| WO | WO-2005/081335 | A1 | 9/2005 |

* cited by examiner

*Primary Examiner* — Porfirio Nazario Gonzalez
(74) *Attorney, Agent, or Firm* — Connolly Bove Lodge & Hutz LLP

(57) ABSTRACT

The present invention describes new metal complexes. Such compounds can be used as functional materials in a variety of different applications which can in the broadest sense be considered part of the electronics industry.

The compounds of the invention have the formulae (1) and (1a).

22 Claims, No Drawings

METAL COMPLEXES AND THEIR USE AS THE EMITTING CONSTITUENT IN ELECTRONIC COMPONENTS, IN PARTICULAR IN ELECTROLUMINESCENT DISPLAY DEVICES

RELATED APPLICATIONS

This application is a national stage application (under 35 U.S.C. §371) of PCT/EP2005/013044 filed Dec. 6, 2005, which claims benefit of European application 04029182.5 filed Dec. 9, 2004.

DESCRIPTION

The present invention describes new materials and mixtures of materials, their use in electroluminescence elements and displays based thereon.

Organometallic compounds, specifically compounds of the $d^8$ metals, will in the near future be used as functional materials in a variety of different applications which can in the broadest sense be considered part of the electronics industry, e.g. in organic electroluminescence devices. The general structure of such devices is described, for example, in U.S. Pat. Nos. 4,539,507 and 5,151,629. An organic electroluminescence device usually consists of a plurality of layers which are applied on top of one another by means of vacuum methods or printing methods. Organic electroluminescence devices (OLEDs) have already been introduced on the market, as the car radios from Pioneer and the mobile telephones from Pioneer and SNMD having an "organic display" demonstrate. Further such products will shortly be introduced.

One development which has taken place in recent years is the use of organometallic complexes which display phosphorescence instead of fluorescence (M. A. Baldo et al., *Appl. Phys. Lett.* 1999, 75, 4-6). For quantum-mechanical reasons, a from one- to four-fold increase in energy efficiency and power efficiency is possible when using organometallic compounds as phosphorescent emitters. Whether this development will become established depends on whether appropriate device compositions which can utilize these advantages (triplet emission=phosphorescence compared to singlet emission=fluorescence) in OLEDs are found. Important conditions here are, in particular, a long operating life and a high thermal stability.

However, OLEDs which display triplet emission still suffer from considerable problems which are in urgent need of improvement. This applies particularly to the triplet emitter itself. Red emitters based on metal complexes which comprise 1-phenylisoquinoline ligands coordinated to iridium as substructures of the formula A and the formula B are known from the literature (e.g. US 2003/0068526, WO 2003/000661). The substructures shown here differ in the absence (formula A) or presence (formula B) of a bridge between the phenyl ring and the isoquinoline ring. This bridge comprises 2-20 alkyl carbon atoms which may be replaced by heteroatoms.

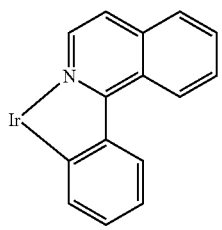

Formula A

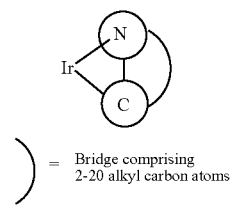

Formula B

) = Bridge comprising 2-20 alkyl carbon atoms

Compounds of this type are suitable as red emitters, but in practice have some critical weak points which make the industrial use of these compounds seem improbable:

1. A critical deficiency is the low thermal stability of the above-described compounds. Thus, for example, the homoleptic complex fac-tris(1-phenylisoquinoline-$C^2$,N)iridium(III) (generally referred to as Ir(piq)$_3$) cannot be sublimed without decomposition. Even under typical high-vacuum conditions (p<$10^{-7}$ mbar), considerable decomposition of this compound is observed, with not only an iridium-containing ash which accounts for about 30% by weight of the amount of Ir(piq)$_3$ used but also the liberation of 1-phenylisoquinoline and other low molecular weight compounds being observed. This thermal decomposition leads to device characteristics having poor reproducibility, with the life being particularly adversely affected. In the purification of the metal complexes by sublimation, too, it would be desirable to have more thermally stable complexes available, since the decomposition leads to large losses of complexes.
2. The operating life is generally still too low, which stands in the way of introduction of phosphorescing OLEDs in high-quality and long-life devices.
3. The complexes frequently have only a low solubility in organic solvents, which makes efficient purification by recrystallization or chromatography much more difficult or impossible. This applies particularly to the purification of relatively large amounts as are required in manufacture of displays.
4. The complexes are very oxidation-sensitive, especially in solution. The purification, storage, transport and processing of these compounds may have to be carried out under inert gas, which is industrially very costly and therefore represents a significant disadvantage.

In particular, a simultaneous improvement in the life and the thermal stability of the complexes would be advantageous. There is therefore a need for compounds which do not suffer from the abovementioned weak points, but are at least equal to the known metal complexes in terms of efficiency and emission colour.

Complexes having improved thermal stability are described in WO 04/081017. However, the synthesis of the ligands of these complexes is very complicated, so that complexes with more readily accessible ligands and also good electronic properties and high thermal stability would be advantageous.

It has now surprisingly been found that particular new compounds which use a six-membered chelate ring in place of the five-membered chelate ring which is generally used and is used in the compounds depicted above have excellent properties as triplet emitters in OLEDs. For illustration, an iridium five-membered chelate and an iridium six-membered chelate are depicted below, with D being a coordinating atom, for example nitrogen, and C being carbon as usual:

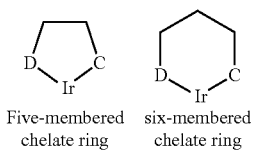

Five-membered chelate ring    six-membered chelate ring

Some metal complexes having six-membered and seven-membered chelate rings for use in OLEDs have been described in the literature:

Thus, EP 1211257 describes metal complexes which have a nonconjugated unit X, for example O, S, $CR_2$, etc., between the phenyl ring and the pyridine ring, which results in formation of chelate complexes having six-membered rings and noncontinuously conjugated ligand systems. These complexes display blue to orange-red emission, as shown by the examples of the abovementioned patent application, but are obviously not suitable for generating deep-red emission, which may be due to the lack of conjugation of the ligand. However, there is at present still a serious lack of compounds having a deep-red emission and good electronic properties and high thermal stability. In addition, a very high operating voltage is required for light-emitting diodes comprising compounds as described in the patent application cited. Thus, for example, a voltage of from 8 to 12 V is reported for blue emission. This is unsuitable for the application and could once again be due to the lack of conjugation of the ligands. It is therefore not possible to see how such six-membered chelate structures could be beneficially used.

JP 2003/342284 describes similar complexes having a six-membered chelate ring in which the unit X is part of a larger ring system. In particular, X is the nitrogen of a carbazole system or a carbon in the 9 position of a fluorene. This once again results in formation of systems whose ligands are non-conjugated. For this reason, the same disadvantages described above can be expected here.

JP 2004/111193 describes conjugated and nonconjugated complexes having seven-membered chelate rings.

The present invention provides compounds of the formula (1)

$$M(L)_n(L')_m(L'')_o \quad \text{Formula (1)}$$

containing a substructure $M(L)_n$ of the formula (2),

Formula (2)

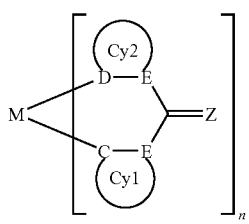

where the symbols and indices used have the following meanings:

M is a transition metal on each occurrence;

D is identical or different on each occurrence and is in each case an $sp^2$-hybridized heteroatom having a nonbonding electron pair which coordinates to M;

C is on each occurrence a $sp^2$-hybridized carbon atom which is bound to M;

E is identical or different on each occurrence and is in each case an $sp^2$-hybridized carbon or nitrogen atom;

Z is identical or different on each occurrence and is in each case $C(R)_2$ or NR;

Cy1 is identical or different on each occurrence and is in each case a homocycle or heterocycle which is bound to M via an $sp^2$-hybridized carbon atom and may have a bond to the group R;

Cy2 is identical or different on each occurrence and is in each case a heterocycle which coordinates to M via the atom D and may have a bond to the group R;

R is identical or different on each occurrence and is in each case H, F, CN, a straight-chain alkyl or alkoxy group having from 1 to 40 carbon atoms or a branched or cyclic alkyl or alkoxy group having from 3 to 40 carbon atoms, where in each case one or more nonadjacent $CH_2$ groups may be replaced by $-R^2C=CR^2-$, $-C\equiv C-$, $Si(R^2)_2$, $Ge(R^2)_2$, $Sn(R^2)_2$, $-O-$, $-S-$, $-NR^2-$, $-(C=O)-$, $-(C=NR^2)-$, $-P=O(R^2)-$, SO, $SO_2$ or $-CONR^2-$ and one or more H atoms may be replaced by F, or an aromatic or heteroaromatic ring system or an aryloxy or heteroaryloxy group having from 5 to 40 aromatic ring atoms which may be substituted by one or more nonaromatic radicals R, or a combination of two, three or four of these systems; with it also being possible for R together with one or both of the rings Cy1 and/or Cy2 to form a further aliphatic, aromatic or heteroaromatic ring system;

$R^2$ is identical or different on each occurrence and is in each case H or an aliphatic or aromatic hydrocarbon radical having from 1 to 30 carbon atoms;

n is 1, 2 or 3;

where the ligands L' and L" in the formula (1) are monoanionic, bidentate chelating ligands; m and o are identical or different on each occurrence and are in each case 0, 1 or 2; and n+m+o=2 or 3.

For the purposes of the present invention, hybridization is the linear combination of atomic orbitals. Thus, linear combination of one 2s and two 2p orbitals forms three equivalent $sp^2$ hybrid orbitals which form an angle of 120° to one another. The remaining p orbital is then capable of forming a $\pi$ bond, for example in an aromatic system.

For the purposes of the present invention, a $C_1$-$C_{40}$-alkyl group in which individual H atoms or $CH_2$ groups may be replaced by the abovementioned groups is particularly preferably one of the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$-$C_{40}$-alkoxy group is particularly preferably methoxy, ethoxy, n-propoxy, i-propoxy, n-butoxy, i-butoxy, s-butoxy, t-butoxy or 2-methylbutoxy. An aromatic or heteroaromatic ring system which has 5-40 aromatic ring atoms and may be substituted by the abovementioned radicals R and can be joined via any positions to the aromatic or heteroaromatic is, in particular, a group derived from benzene, naphthalene, anthracene, phenanthrene, pyrene, chrysene, perylene, fluoranthene, naphthacene, pentacene, benzpyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazote, naphthoxazole, anthroxazole, phenanthroxazole, isoxazole, 1,2-thiazole, 1,3-thiazole, benzothiazole, pyridazine, benzopyridazine, pyrimidine, benzpyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Cy1 and Cy2, are preferably aromatic or heteroaromatic systems. Furthermore, further cyclic, aliphatic or aromatic systems can also be fused onto Cy1 and Cy2 and/or Cy1 and/or Cy2 can, of course, also be substituted. Here, preferred substituents are the radicals $R^1$ described below.

Preference is given to compounds of the formula (1), containing a substructure $M(L)_n$ of the formula (2a),

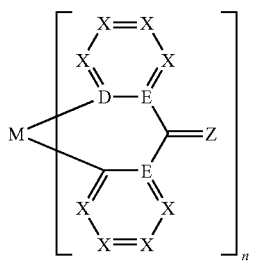

Formula (2a)

where Z, $R^2$, L', L", n, m and o are as defined above and the further symbols have the following meanings:

M is Mo, W, Re, Ru, Os, Rh, Ir, Pd, Pt or Au on each occurrence;

D is identical or different on each occurrence and is in each case nitrogen or phosphorus;

X is identical or different on each occurrence and is in each case $CR^1$, N or P; or (X—X) or (X=X)
(i.e. two adjacent radicals X) represents $NR^1$, S or O, with the proviso that Cy1 and Cy2 each form a five- or six-membered ring; or (X—X) or (X=X)
(i.e. two adjacent radicals X) represents $CR^1$, N or P if the symbol E in the corresponding ring represent N;

E is identical or different on each occurrence and is in each case C or N, with the proviso that, if the symbol E represents N, precisely one unit (X—X) (i.e. two adjacent radicals X) in the corresponding ring is $CR^1$, N or P, so that the ring is then a five-membered ring;

R is as defined above and may also form a ring system together with X or with $R^1$;

$R^1$ is identical or different on each occurrence and is in each case H, F, Cl, Br, I, OH, $NO_2$, CN, $N(R^2)_2$, a straight-chain alkyl, alkoxy or thioalkoxy group having from 1 to 40 carbon atoms or a branched or cyclic alkyl, alkoxy or thioalkoxy group having from 3 to 40 carbon atoms, where one or more nonadjacent $CH_2$ groups may be replaced by —$R^2C=CR^2$—, —C≡C—, $Si(R^2)_2$, $Ge(R^2)_2$, $Sn(R^2)_2$, —O—, —S—, —$NR^2$—, —(C=O)—, —(C=$NR^1$)—, —P=O($R^2$)—, SO, $SO_2$, —$COOR^2$— or —$CONR^2$— and one or more H atoms may be replaced by F, Cl, Br, I or CN, or an aromatic or heteroaromatic ring system or an aryloxy or heteroaryloxy group which has from 5 to 40 aromatic ring atoms and may be substituted by one or more nonaromatic radicals $R^1$, or a combination of two, three or four of these systems; with a plurality of substituents $R^1$, either on the same ring or on different rings, or $R^1$ and R and/or $R^2$ may together form a further monocyclic or polycyclic, aliphatic, aromatic or heteroaromatic ring system.

A particularly preferred embodiment of the present invention provides compounds of the formula (1a),

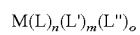

Formula (1a)

containing at least one substructure $M(L)_n$ of the formula (2b), identical or different on each occurrence,

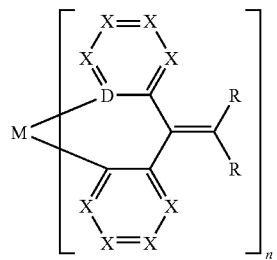

Formula (2b)

and possibly containing a substructure $M(L')_m$ of the formula (3), identical or different on each occurrence,

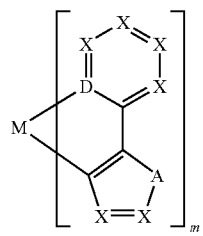

Formula (3)

where M, D, R, $R^1$, $R^2$, L", n, m and o are as defined above and the further symbols have the following meanings:

X is identical or different on each occurrence and is in each case $CR^1$, N or P; or (X—X) or (X=X)
(i.e. two adjacent radicals X) represents $NR^1$, S or O, with the proviso that Cy1 and Cy2 each form a five- or six-membered ring;

A is identical or different on each occurrence and is in each case —$CR^1$=$CR^1$—, —N=$CR^1$—, —P=$CR^1$—, —N=N—, —P=N—, $NR^1$, $PR^1$, O, S or Se.

Very particular preference is given to compounds of the formula (1) or the formula (1a) containing a substructure $M(L)_n$ of the formula (2c), of the formula (2d) or of the formula (2e),

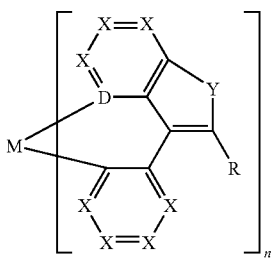

Formula (2c)

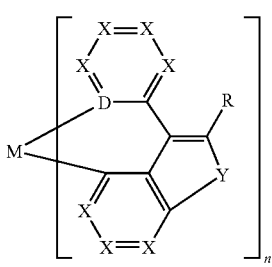

Formula (2d)

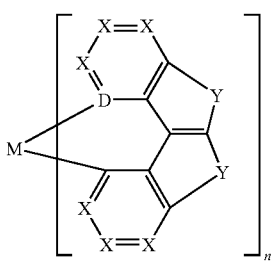

Formula (2e)

where M, X, D, R, $R^1$, $R^2$ and n are as defined above, and the symbol Y has the following meanings:

Y is identical or different on each occurrence and is in each case a bivalent group selected from among —C($R^1$)$_2$—, —C(=O)—, —C[=C($R^1$)$_2$]—, —C($R^1$)$_2$—C($R^1$)$_2$—, —C(=O)—O—, —C(=O)—N($R^1$)—, —C($R^1$)$_2$—C($R^1$)$_2$—C($R^1$)$_2$—, —C($R^1$)$_2$—O—C($R^1$)$_2$—, —C($R^1$)$_2$—N($R^1$)—, —C($R^1$)=C($R^1$)—, —C($R^1$)=N—, —O—, —S—, —N($R^1$)—, —P($R^1$)—, —P(=O)($R^1$)— and —B($R^1$)—.

Monoanionic, bidentate ligands L" which are suitable for the purposes of the invention are 1,3-diketonates derived from 1,3-diketones such as acetylacetone, benzoylacetone, 1,5-diphenylacetylacetone, bis(1,1,1-trifluoroacetyl)methane, 3-ketonates derived from 3-keto esters such as ethyl acetoacetate, carboxylates derived from aminocarboxylic acids such as pyridine-2-carboxylic acid, quinoline-2-carboxylic acid, glycine, N,N-dimethylglycine, alanine, N,N-dimethylalanine, salicyliminates derived from salicylimines such as methylsalicylimine, ethylsalicylimine, phenylsalicylimine, and also borates of nitrogen-containing heterocycles, e.g. tetrakis(1-imidazolyl)borate and tetrakis(1-pyrazolyl)borate.

The ligands L are either conjugated or cross-conjugated systems. Conjugated systems are produced when at least one of the substituents R together with the ring Cy1 and/or Cy2 forms an aromatic ring system. On the other hand, cross-conjugated systems are produced when none of the substituents R together with Cy1 or Cy2 forms an aromatic ring system, i.e. when R forms either an aliphatic ring system or no ring system at all together with Cy1 or Cy2.

In a particularly preferred embodiment of the invention, the ligand systems are stiff systems, i.e. systems in which the two substituents R together with the ring Cy1 and ring Cy2 form a five-membered ring or a six-membered ring as in the formula (2e).

In a further particularly preferred embodiment of the invention, the ligand has a structure and substitution pattern such that no five-membered chelate ring can be formed on coordination to a metal.

Preference is also given to compounds of the formula (1) or the formula (1a) in which the symbol M=Rh, Ir, Pd or Pt; particular preference is given to M=Ir or Pt and very particular preference is given to M=Ir.

Preference is also given to compounds of the formula (1) or the formula (1a) in which the symbol n=2 or 3. Particular preference is given to compounds in which the symbol o=0. Very particular preference is given to compounds in which the symbols m=o=0. In particular, n=2 and m=o=0 in the case of palladium and platinum complexes and other metals having square planar coordination and n=3 and m=o=0 in the case of rhodium and iridium complexes and other metals having octahedral coordination.

Preference is also given to compounds of the formula (1) or the formula (1a) in which the symbol Z=C(R)$_2$.

Preference is also given to compounds of the formula (1) or the formula (1a) in which the symbol D=N.

Preference is also given to compounds of the formula (1) or the formula (1a) in which the symbol X=$CR^1$ or N, in particular X=$CR^1$.

Preference is given to the inventive compounds of the formula (1) or formula (1a) in which the symbol Y in the formulae (2c), (2d) and (2e) is a bivalent group selected from among —C($R^1$)$_2$—, —C(=O)—, —C($R^1$)$_2$—C($R^1$)$_2$—, —C($R^1$)$_2$—N($R^1$)—, —C($R^1$)=C($R^1$)—, —C($R^1$)=N—, —O—, —S— and —N($R^1$)—. The symbol Y is particularly preferably —C($R^1$)$_2$—, —C($R^1$)$_2$—C($R^1$)$_2$—, —C($R^1$)=C($R^1$)—, —S— or —N($R^1$)—.

In a further preferred embodiment of the invention, two or three ligands L and/or L' and/or L" can be joined via the radicals R' to form a polypodal system or a cryptand. The link in this case can be either to Cy1 or Cy2.

The corresponding ligands which produce the substructures of the formula (2) or the formulae (2a) to (2e) and also the ligands L' and L" can be prepared by customary methods of organic chemistry as are known to those skilled in the art of organic synthesis. Fully bridged systems, i.e. systems in which two groups Y of the formula (2e) are present, are suitable for the ligand synthesis by reactions analogous to those described in the literature (e.g. A.-S. Rebstock et al, *Tetrahedron* 2003, 59, 4973-4977; R. G. Harvey et al, *J. Org. Chem.* 2000, 65, 3952-3960).

The metal complexes of the invention can in principle be prepared by various methods, but the processes described below have been found to be particularly useful.

The present invention therefore also provides a process for preparing metal complexes by reacting the corresponding free ligands with metal alkoxides of the formula (4), with metal ketoketonates of the formula (5) or mononuclear or multinuclear metal halides of the formula (6), (7) or (8), M(OR²)₃    Formula (4)

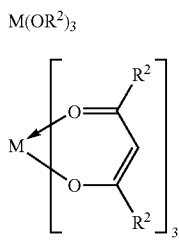    Formula (5)

MHal₃    Formula (6)

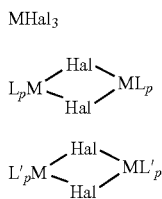    Formula (7)

Formula (8)

where the symbols M and R² are as defined above, p=1 or 2 and Hal=F, Cl, Br or I.

Furthermore, the use of metal compounds, preferably rhodium and iridium compounds, which bear both alkoxide and/or halide and/or hydroxy and ketoketonate radicals is also particularly preferred. These compounds can also be charged. Iridium compounds of this type which are particularly suitable as starting materials are disclosed in WO 04/085449, for example Na[Ir(acac)₂Cl₂].

The synthesis of the complexes is preferably carried out as described in WO 02/060910 and in WO 04/085449. Heteroleptic complexes can, for example, also be synthesized as described in WO 05/042548.

These methods enable the inventive compounds of the formula (1) to be obtained in high purity, preferably more than 99% (determined by means of ¹H-NMR and/or HPLC).

The synthetic methods described here can be used to prepare, inter alia, the structures (1) to (141) depicted below for the compounds of the formula (1), and these can be further substituted by substituents R¹. The substituents are not shown in some cases in the interests of clarity.

(1)

(2)

(3)

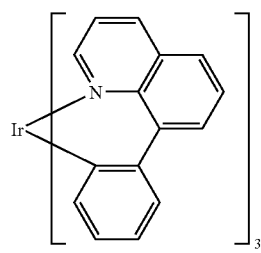

(4)

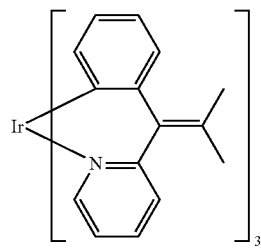

(5)

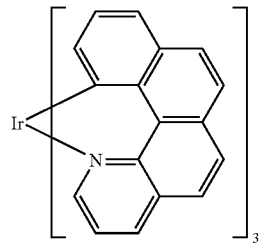

(6)

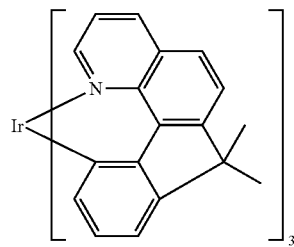

(7)

(8)

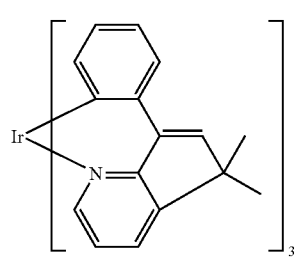

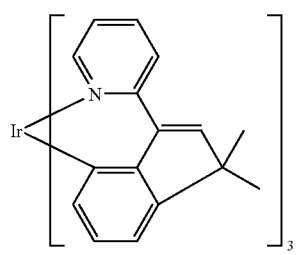
(9)
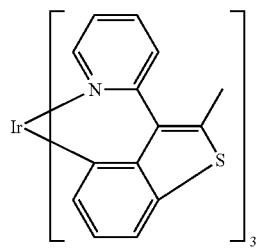
(10)
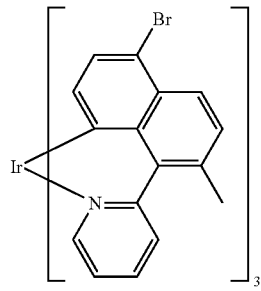
(11)
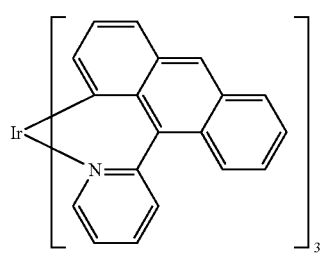
(12)
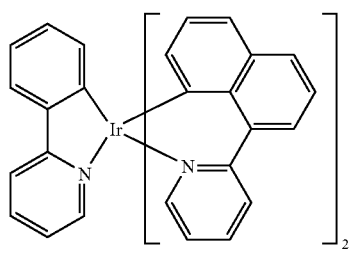
(13)
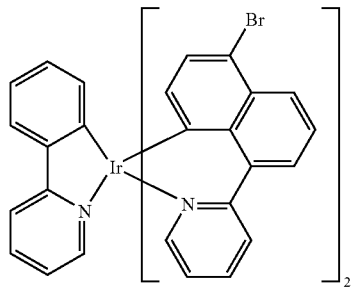
(14)
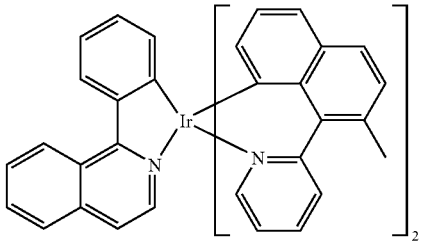
(15)
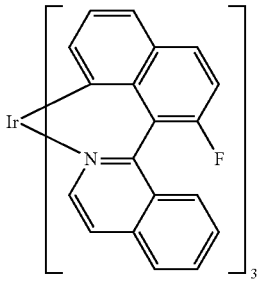
(16)
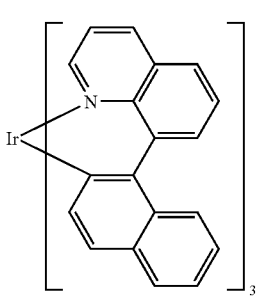
(17)
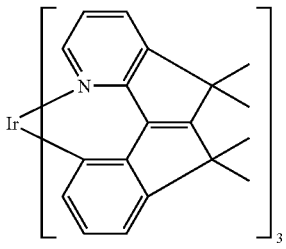
(18)
(19)
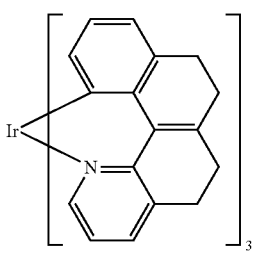
(20)

(21) 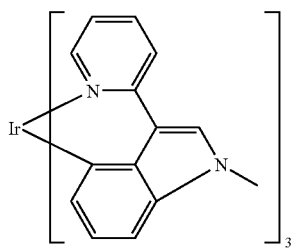
(22) 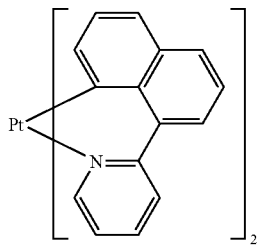
(23) 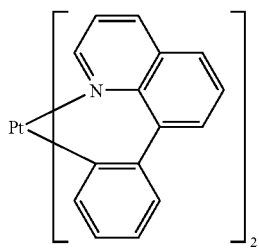
(24) 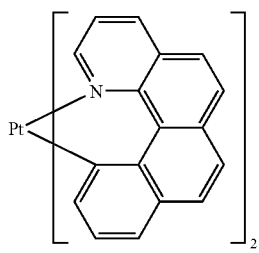
(25) 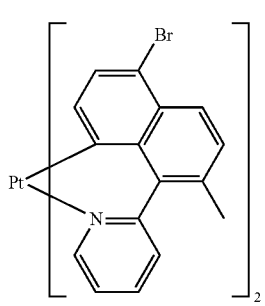
(26) 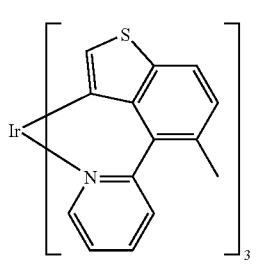
(27) 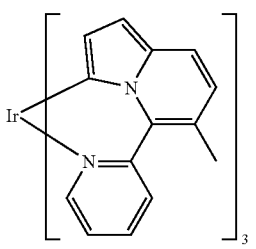
(28) 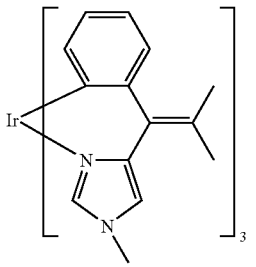
(29) 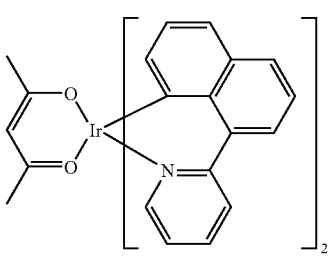
(30) 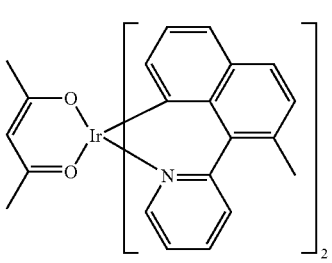
(31) 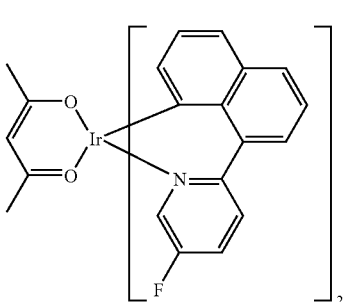
(32) 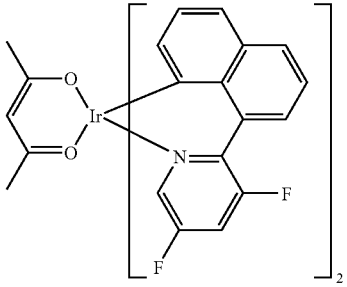

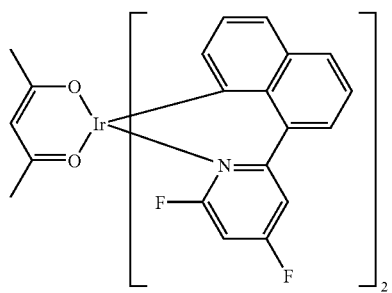
(33)
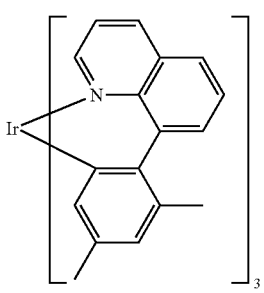
(38)
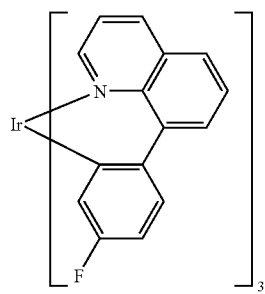
(34)
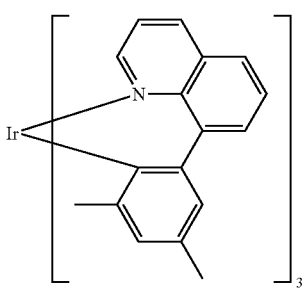
(39)
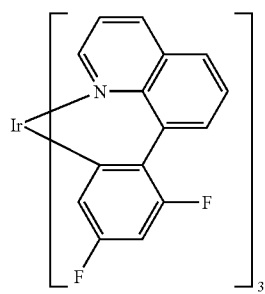
(35)
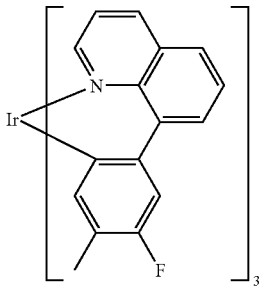
(40)
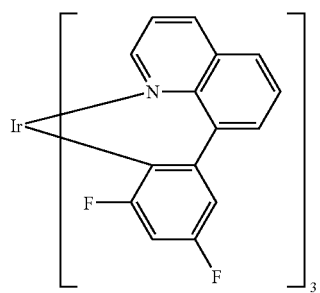
(36)
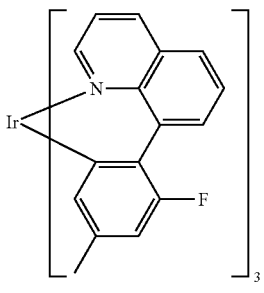
(41)
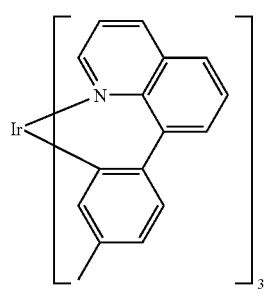
(37)
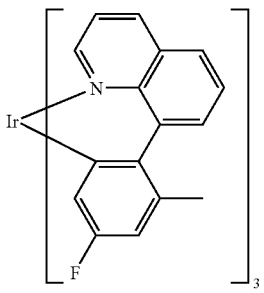
(42)

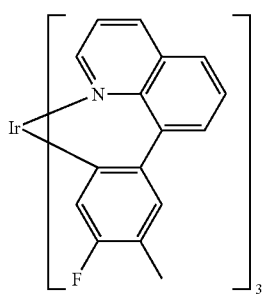
(43)
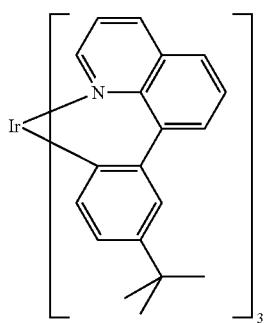
(44)
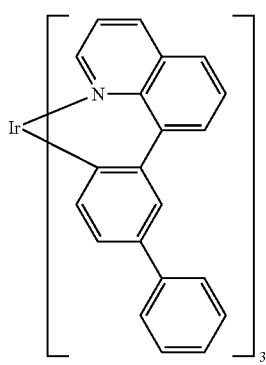
(45)
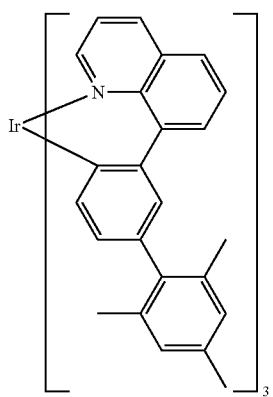
(46)

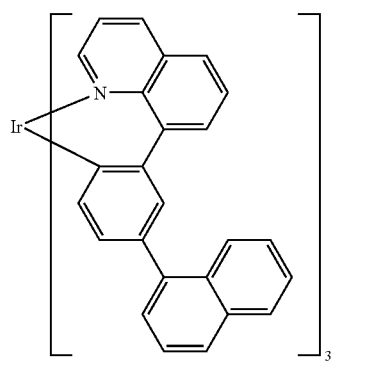
(50)
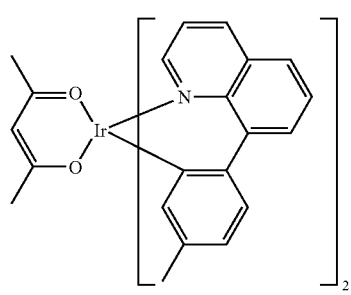
(51)
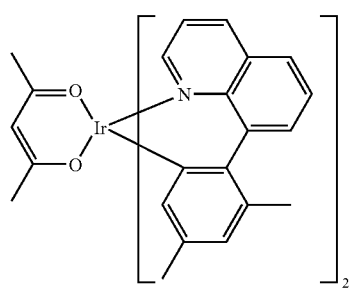
(52)
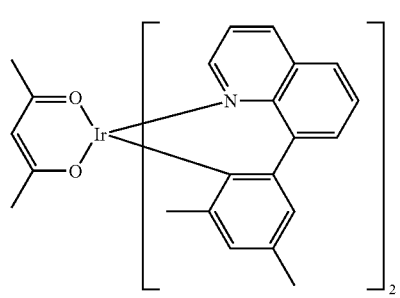
(53)
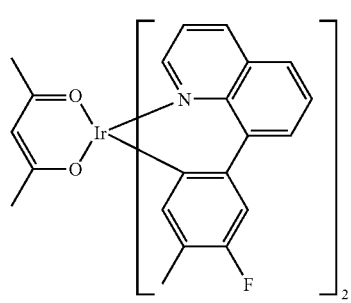
(54)
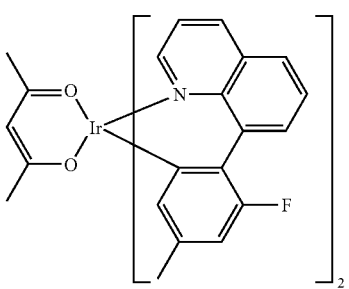
(55)
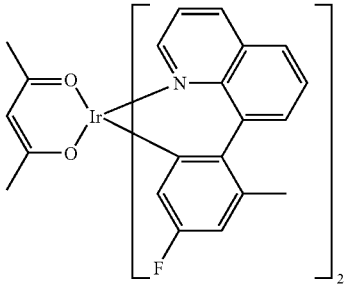
(56)
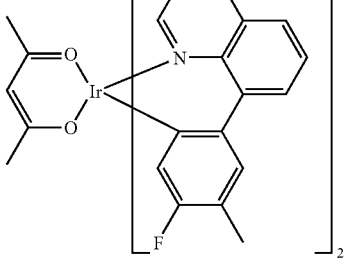
(57)
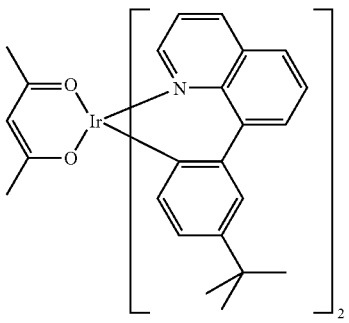
(58)
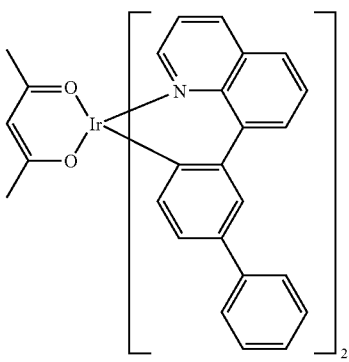
(59)

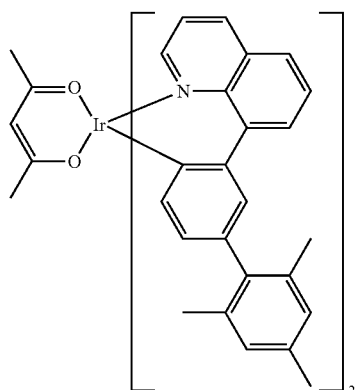
(60)
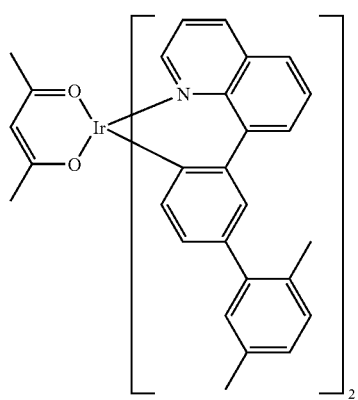
(61)
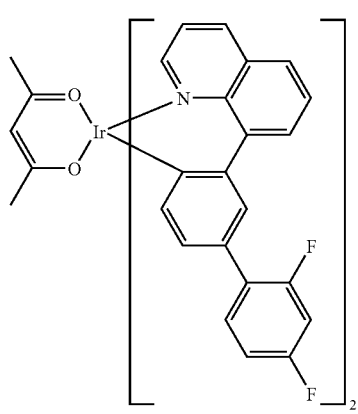
(62)
(64)
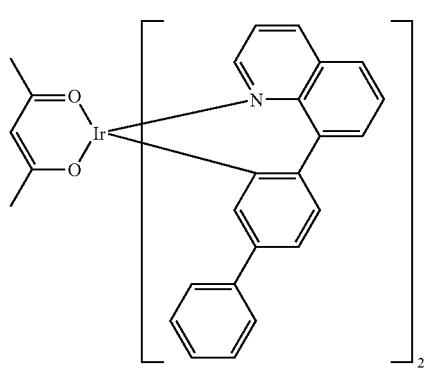
(65)
(66)
(67)
(68)
(69)

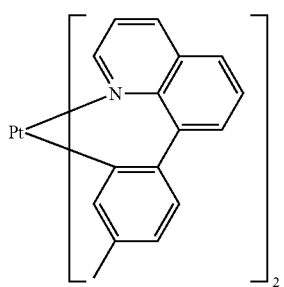 (70)
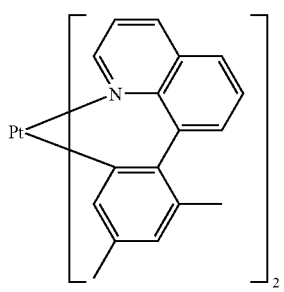 (71)
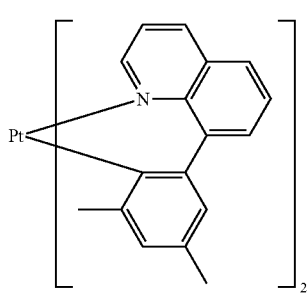 (72)
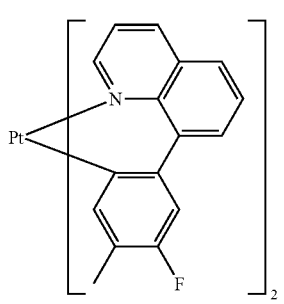 (73)
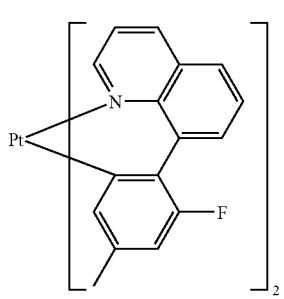 (74)
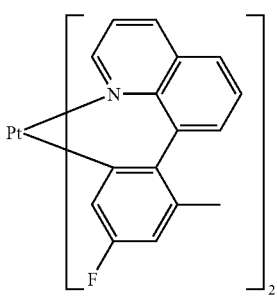 (75)
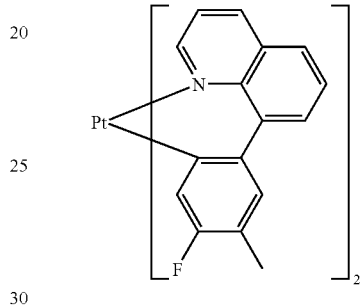 (76)
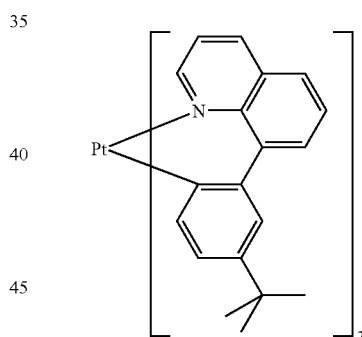 (77)
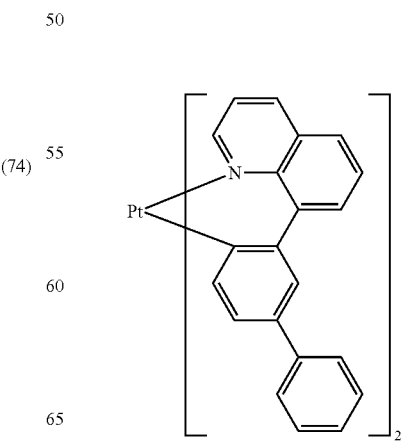 (78)

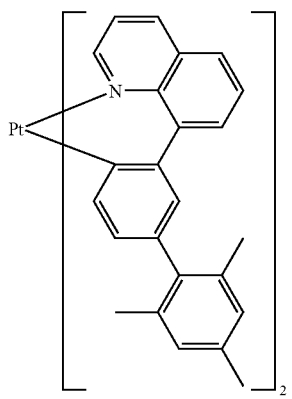
(79)
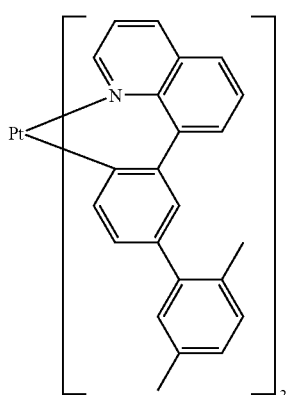
(80)
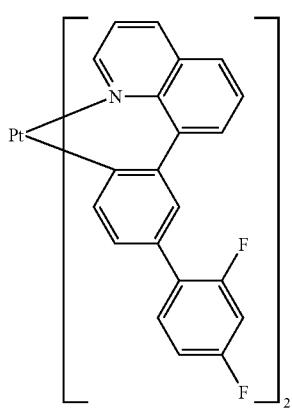
(81)
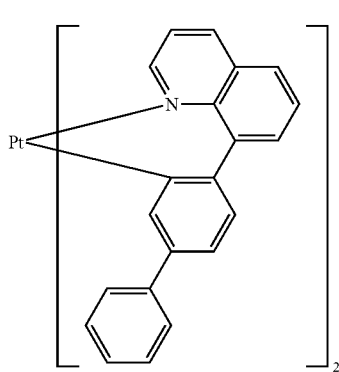
(82)
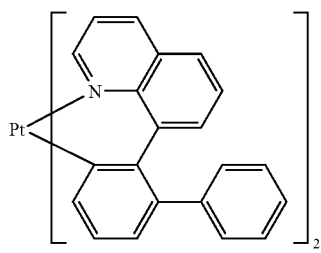
(83)
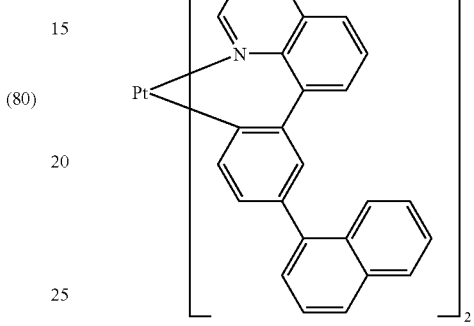
(84)
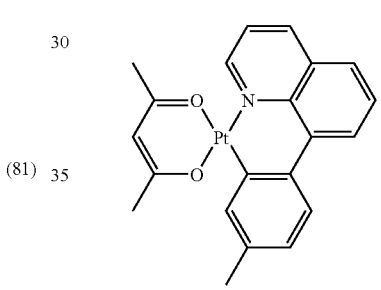
(85)
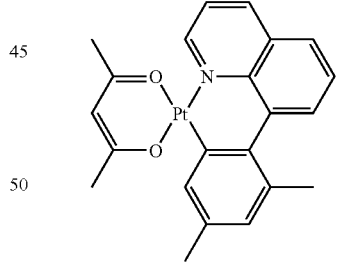
(86)
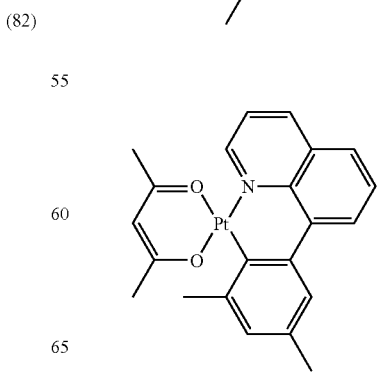
(87)

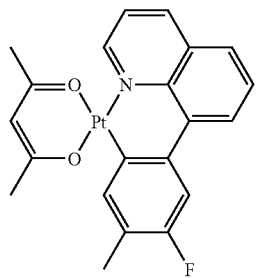
(88)
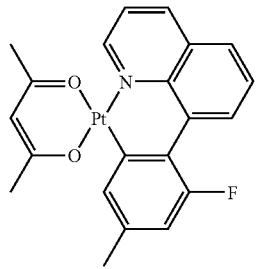
(89)
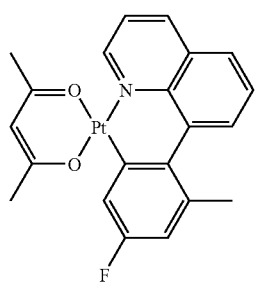
(90)
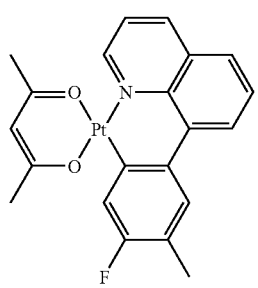
(91)
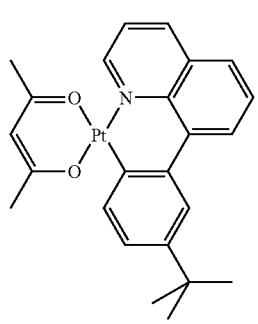
(92)
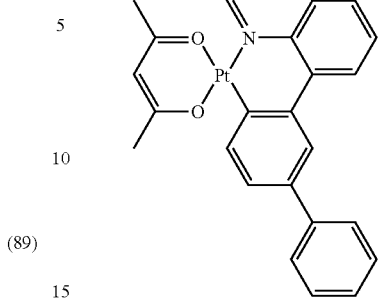
(93)
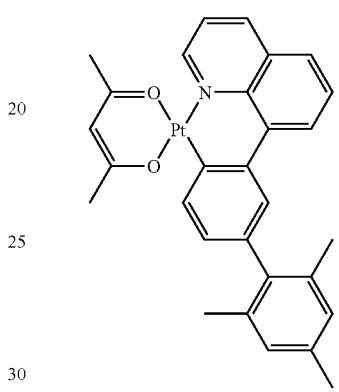
(94)
(95)
(96)

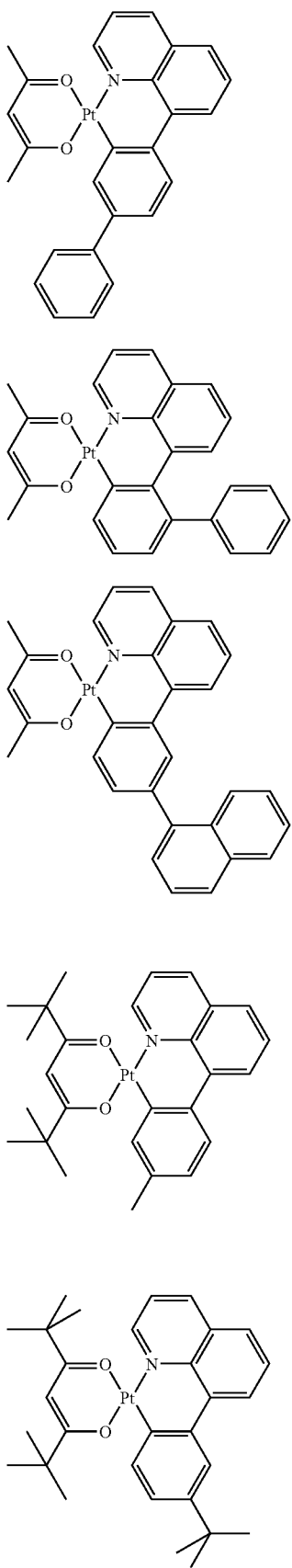
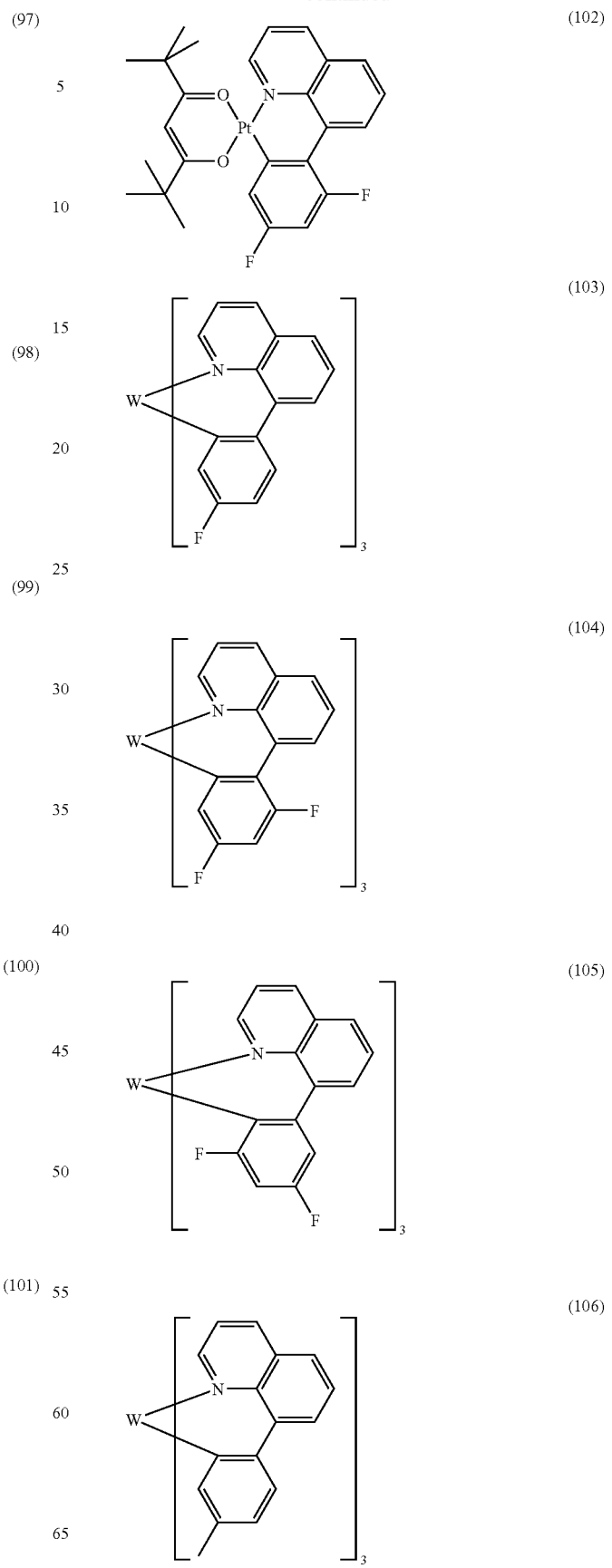

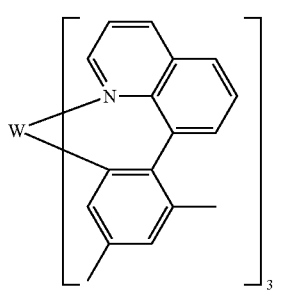
(107)
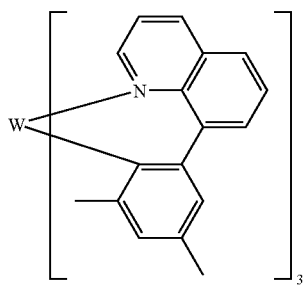
(108)
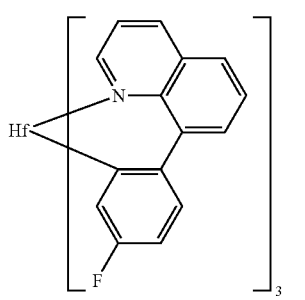
(109)
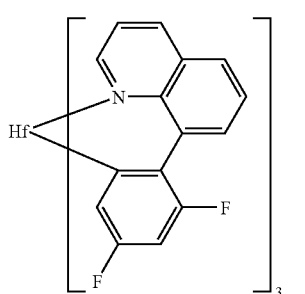
(110)
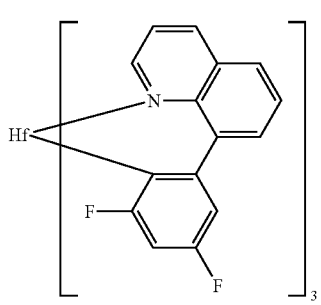
(111)
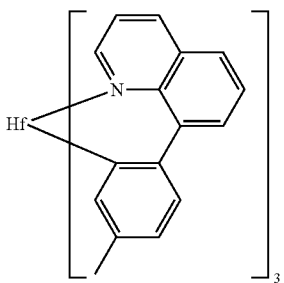
(112)
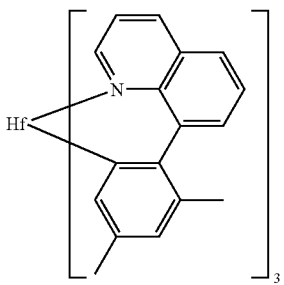
(113)
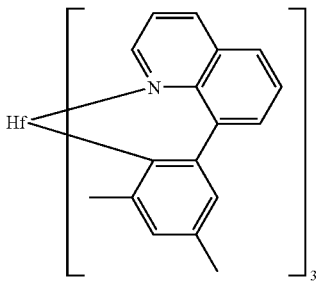
(114)
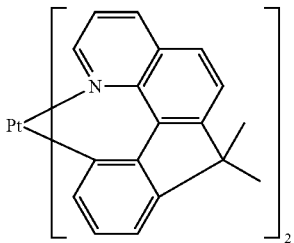
(115)
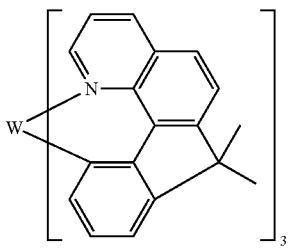
(116)
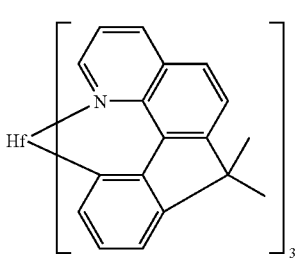
(117)

(118) 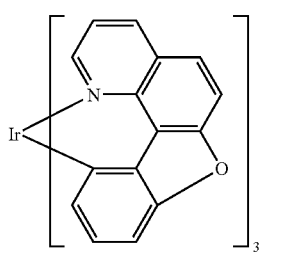
(119) 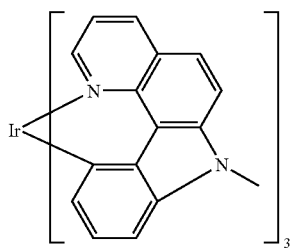
(120) 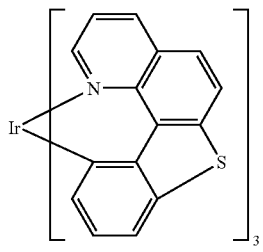
(121) 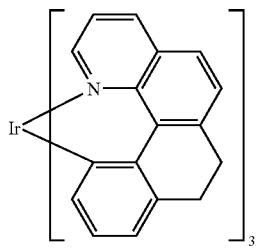
(122) 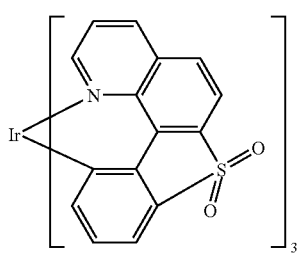
(123) 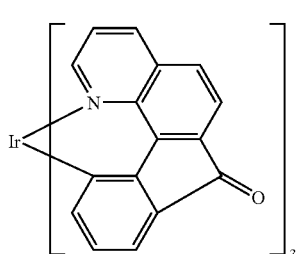
(124) 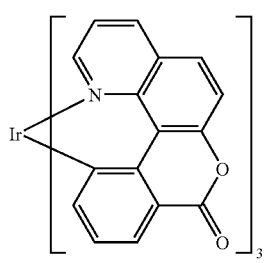
(125) 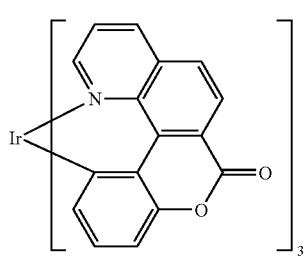
(126) 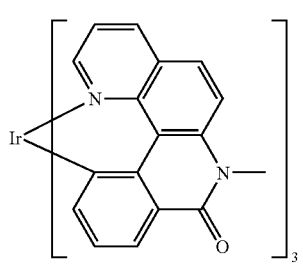
(127) 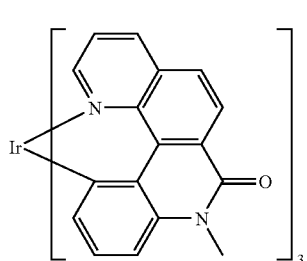
(128) 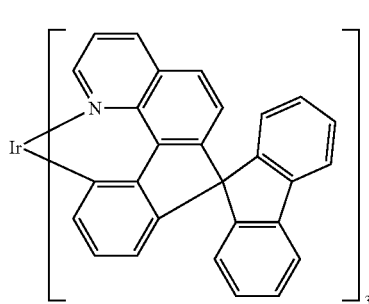
(129) 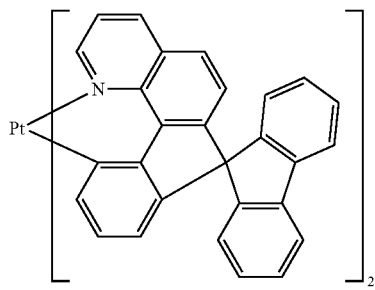

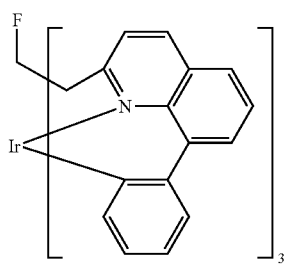 (130)
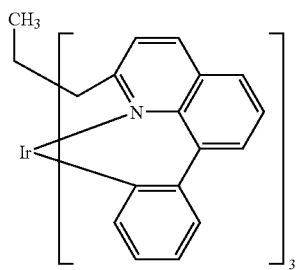 (131)
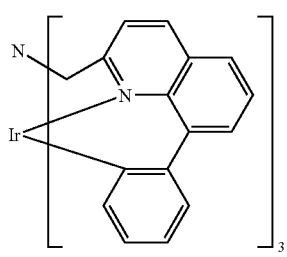 (132)
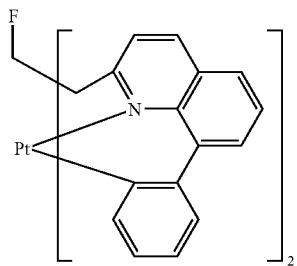 (133)
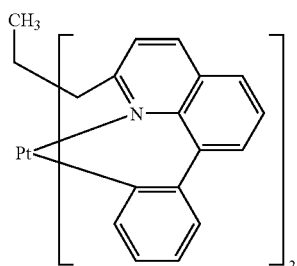 (134)
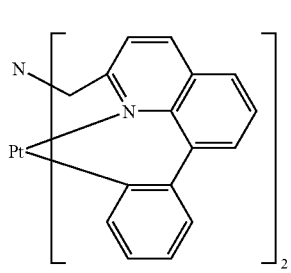 (135)
(136)
(137)
(138)
(139)
(140)

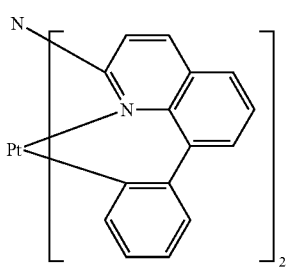
(141)

The inventive compounds described above, e.g. compounds having the structures (11), (14) and (25), can also be used as comonomers for producing corresponding conjugated, partly conjugated or nonconjugated oligomers, polymers or dendrimers. The polymerization is preferably effected via the bromine functionality. Thus, they can be copolymerized into, inter alia, polyfluorenes (e.g. as described in EP 842208 or WO 00/22026), polyspirobifluorenes (e.g. as described in EP 707020 or EP 894107), poly-para-phenylenes (e.g. as described in WO 92/18552), polydihydrophenanthrenes (e.g. as described in WO 05/014689), polyphenanthrenes (e.g. as described in the unpublished patent application DE 102004020298.2), polyindenofluorenes (e.g. as described in WO 04/041901 and WO 04/113412), polycarbazoles (e.g. as described in WO 04/070772 or WO 04/113468), polyketones (e.g. as described in WO 05/040302), polysilanes (e.g. as described in DE 102004023278.4) or polythiophenes (e.g. as described in EP 1028136) or into copolymers comprising various units of these types. These units can either be built into the side chain or into the main chain of the polymer or can also represent branching points of the polymer chains (e.g. as described in DE 102004032527.8) or the end groups of the polymer chain.

The invention therefore also provides for the use of compounds of the formula (1) or of the formula (1a) in which at least one of the substituents $R^1$ is a group which is capable of a C—C coupling reaction catalyzed by palladium or nickel for the synthesis of conjugated, partly conjugated or nonconjugated polymers, oligomers or dendrimers. The substituent which is capable of a C—C coupling reaction is preferably selected from the group consisting of Cl, Br, I, O-tosylate, O-triflate, O—$SO_2R^2$, $B(OR^2)_2$ and $Sn(R^2)_3$, particularly preferably from among Br, O-triflate and $B(OR^2)_2$, where $R^2$ is as defined above and two or more radicals $R^2$ may together also form a ring system. Preference is also given to this group being bound to the ring Cy1, particularly preferably in the para position relative to the bond to the metal M. These metal complexes which can be used as monomers for the polymerization are likewise a preferred embodiment of the present invention.

Regardless of whether this group which is capable of the C—C coupling reaction is present once, twice or three times or more often in the complex, the complex represents an end group in the polymer or it is incorporated linearly into the polymer chain, or it represents a branching point of the polymer chain. Furthermore, the complex can also, if appropriately substituted, be a side chain or a linear or branched polymer chain.

The invention thus also provides conjugated, partly conjugated or nonconjugated oligomers, polymers or dendrimers comprising one or more of the compound of the formula (1) or the formula (1a), with at least one of the above-defined radicals R and $R^1$, preferably $R^1$, representing a bond to the oligomer, polymer or dendrimer. The same preferences as described above apply to units of the formula (1) or the formula (1a) in polymers and dendrimers.

The abovementioned oligomers, polymers, copolymers and dendrimers display good solubility in organic solvents and a high efficiency and stability in organic electroluminescent devices. Furthermore, these oligomers, polymers and dendrimers are very thermally stable.

Furthermore, the inventive compounds of the formula (1), in particular those which are functionalized by halogens, can also be further functionalized by means of customary types of reactions and thus converted into expanded compounds of the formula (1). An example which may be mentioned is functionalization with arylboronic acids using the Suzuki method or by amines using the Hartwig-Buchwald method.

The inventive compounds, oligomers, polymers, dendrimers or expanded compounds of the formula (1) are used as active components in electronic components such as organic light-emitting diodes (OLEDs), organic integrated circuits (O-ICs), organic field effect transistors (O-FETs), organic thin film transistors (O-TFTs), organic solar cells (O-SCs), organic light-emitting transistors (O-LETs), organic field quench devices (O-FQDs), light-emitting electrochemical cells (LECs) or organic laser diodes (O-lasers).

The present invention therefore also provides for the use of the inventive compounds of the formula (1), the inventive oligomers, polymers and dendrimers and corresponding expanded compounds of the formula (1) as active component in electronic components, in particular as light-emitting compound.

The invention further provides electronic components, in particular organic and polymeric light-emitting diodes (OLEDs, PLEDs), organic field effect transistors (O-FETs), organic thin film transistors (O-TFTs), organic integrated circuits (O-ICs), organic solar cells (O-SCs), organic light-emitting transistors (O-LETs), organic field quench devices (O-FQDs), light-emitting electrochemical cells (LECs) and organic laser diodes (O-lasers), comprising one or more inventive compounds of the formula (1), inventive oligomers, polymers and dendrimers and corresponding expanded compounds of the formula (1), in particular as emitting compound.

The compounds of the invention are preferably used as emitting compounds in an emitting layer in an organic or polymeric light-emitting diode. Particularly when the compounds according to the invention are low molecular weight compounds, they are usually used together with a matrix material. The matrix material can either have a low molecular weight or be oligomeric or polymeric.

Preferred matrix materials are ones based on carbazoles, for example CBP (bis(carbazolyl)biphenyl) or other materials comprising carbazole or carbazole derivatives, e.g. as described in WO 00/057676, EP 01/202358 and WO 02/074015. Preference is also given to ketones and imines, as described, for example, in WO 04/093207, in particular ones based on spirobifluorene, and phosphine oxides, phosphine selenides, phosphazenes, sulphoxides and sulphones, as described, for example, in WO 05/003253, in particular ones based on spirobifluorene. Preference is also given to silanes, polypodal metal complexes, e.g. as described in WO 04/081017, and oligophenylenes based on spirobifluorenes, e.g. as described in EP 676461 and WO 99/40051. Particularly preferred matrix materials are ketones, phosphine oxides, sulphoxides and sulphones. Very particular preference is given to ketones and phosphine oxides.

The compounds of the invention have the following advantages over compounds according to the prior art:
1. The compounds of the invention have a high thermal stability. Thus, the low molecular weight compounds can be vaporized in a high vacuum without decomposition, and the oligomeric, dendritic and polymeric compounds are also very thermally stable, so that the devices can be treated thermally without damage. This property is a basic prerequisite for reproducible production of OLEDs and has, in particular, a positive effect on the operating life. Furthermore, resource-conserving utilization of compounds of these rare metals is thus possible, since the complexes can be sublimed virtually without losses in the purification and production of devices.
2. The compounds of the invention display a good solubility in organic solvents, which makes their purification by means of customary methods such as recrystallization or chromatography considerably easier. The compounds can thus also be processed from solution by means of coating or printing techniques. This property is also advantageous in the customary processing by vaporization, since cleaning of the equipment or the shadow masks used is made considerably easier as a result.
3. The compounds of the invention display improved oxidation stability, which has a positive effect on purification and generally on the handling of these compounds.
4. The compounds of the invention can be prepared reproducibly in high purity and display no batch-to-batch variation. An industrial process for producing the electroluminescence devices of the invention is therefore significantly more efficient.
5. The synthesis of the ligands is simpler and comprises fewer steps than the synthesis of the ligands in WO 04/081017. This is a significant industrial advantage.

The present invention is illustrated by the following examples without being restricted thereto. A person skilled in the art will be able to prepare further compounds according to the invention or use these in organic electronic devices on the basis of the information given without making a further inventive step.

EXAMPLES

The following syntheses are, unless indicated otherwise, carried out under a protective gas atmosphere. The starting materials can be procured from the companies ALDRICH or ABCR. The synthesis of 2,7-dibromo-9,9-dimethylfluorene can be carried out as described in EP 1298117, that of 8-quinolinyl trifluoromethanesulphonate can be carried out as described in Organometallics 2005, 24(6), 1329, and that of Na[Ir(acac)Cl$_2$] can be carried out as described in WO 04/085449.

Example 1

(1,3-Pentanedionato-κO,κO')bis[2-(8-quinolinyl-κN) phenyl-κC]iridium(III) (Ir1)

a) Synthesis of 8-phenylquinoline

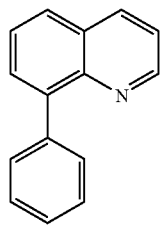

A well stirred suspension of 13.9 g (50 mmol) of 8-quinolinyl trifluoromethane-sulphonate, 12.2 g (100 mmol) of benzeneboronic acid, 8.5 g (200 mmol) of lithium chloride, 8.0 g (75 mmol) of sodium carbonate in a mixture of 200 ml of toluene, 50 ml of dioxane and 50 ml of water is admixed with 1.7 g (1.5 mmol) of tetrakistri-phenylphosphinopalladium(0) and the mixture is refluxed for 16 hours. After cooling, the aqueous phase is separated off, the organic phase is washed three times with 200 ml of water, dried over magnesium sulphate and evaporated to dryness. The oil which remains is recrystallized twice from ethanol (5 ml/g). The yield at a purity of 99.0% according to $^1$H-NMR is 8.6 g (42 mmol), corresponding to 83.8% of theory.

$^1$H-NMR (CDCl$_3$): δ [ppm]=8.94 (d, 1H), 8.20 (d, 1H), 7.81 (d, 1H), 7.75-7.70 (m, 2H), 7.60 (dd, 1H), 7.52 (dd, 1H), 7.45-7.40 (m, 4H).

b) Synthesis of (1,3-pentanedionato-κO,κO')bis[2-(8-quinolinyl-κN)phenyl-κC]iridium(III) (Ir1)

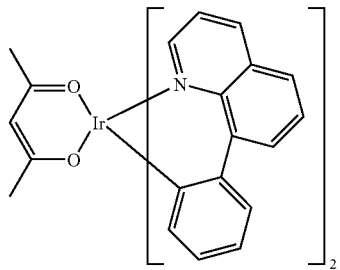

A mixture of 1.76 g (5.0 mmol) of iridium(III) chloride hydrate, 2.26 g (11.0 mmol) of 8-phenylquinoline, 75 ml of 2-ethoxyethanol and 25 ml of water is refluxed for 48 hours. The reaction mixture is evaporated under reduced pressure, the brown residue is taken up in a mixture of 200 ml of water and 100 ml of ethanol and stirred at 60° C. for 1 hour. The solid is filtered off with suction and washed three times with 100 ml each time of ethanol. The brown solid is then suspended in 50 ml of ethoxyethanol, admixed with 0.72 ml (7.0 mmol) of acetylacetone and 1.11 g (8.0 mmol) of potassium carbonate and refluxed for 16 hours. After cooling, the dark red precipitate is filtered off with suction, washed three times with 100 ml each time of a mixture of ethanol/water (1:1, v:v) and then washed three times with 100 ml of ethanol. After drying, the precipitate is dissolved in 200 ml of dichloromethane. The solution is filtered through silica get, evaporated to a volume of 50 ml and then admixed with 100 ml of n-heptane. Renewed recrystallization from dichloro-methane/n-heptane gives 1.87 g (2.6 mmol), corresponding to 53.2% of theory, at a purity of 99.5% according to $^1$H-NMR.

$^1$H-NMR (CDCl$_3$): δ [ppm]=8.57 (d, 2H), 8.35 (d, 2H), 8.10 (d, 2H), 7.71 (d, 2H), 7.65-7.63 (m, 4H), 7.06 (dd, 2H), 6.96 (d, 2H), 6.72-6.66 (m, 4H), 4.25 (s, 1H), 1.09 (s, 6H).

Example 2

(1,3-Pentanedionato-κO,κO')bis[2-(8-quinolinyl-κN) (5-fluoro-phenyl)-κC]iridium(III), (Ir2)

a) Synthesis of 8-(4-fluorophenyl)quinoline

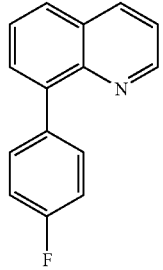

The procedure of Example 1 is repeated using 14.0 g (100 mmol) of 4-fluorobenzeneboronic acid instead of benzeneboronic acid. The yield at a purity of 99.5% according to $^1$H-NMR is 8.4 g (37.5 mmol), corresponding to 75.0% of theory.

$^1$H-NMR (CDCl$_3$): δ [ppm]=8.93 (dd, 1H), 8.19 (dd, 1H), 7.83 (dd, 1H), 7.70 (d, 1H), 7.68-7.64 (m, 4H), 7.60 (dd, 1H), 7.40 (dd, 1H).

b) Synthesis of (1,3-pentanedionato-κO,κO')bis[2-(8-quinolinyl-κN)(5-fluorophenyl)-κC]iridium(III) (Ir2)

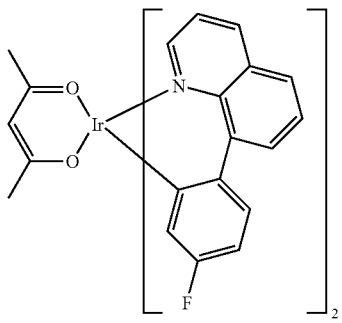

The procedure of Example 1 is repeated using 2.46 g (11.0 mmol) of 8-(4-fluorophenyl)quinoline instead of 8-phenylquinoline. The yield at a purity of 99.5% according to $^1$H-NMR is 1.80 g (2.5 mmol), corresponding to 48.9% of theory.

$^1$H-NMR (CDCl$_3$): δ [ppm]=8.51 (d, 2H), 8.24 (dd, 2H), 8.09 (dd, 2H), 7.66-7.61 (m, 6H), 6.99 (dd, 2H), 6.74 (ddd, 2H), 6.30 (dd, 2H), 4.25 (s, 1H), 1.06 (s, 6H).

Example 3

(1,3-Pentanedionato-κO,κO')bis[2-(8-quinolinyl-κN)(3,5-difluoro-phenyl)-κC]iridium(III) (Ir3)

a) Synthesis of 8-(2,4-difluorophenyl)quinoline

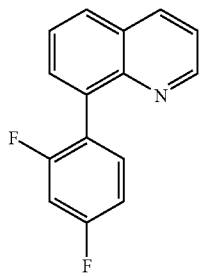

The procedure of Example 1 is repeated using 15.8 g (100 mmol) of 2,4-difluorobenzeneboronic acid instead of benzeneboronic acid. The yield at a purity of 99.0% according to $^1$H-NMR is 9.3 g (38.5 mmol), corresponding to 77.1% of theory.

$^1$H-NMR (CDCl$_3$): δ [ppm]=8.91 (dd, 1H), 8.16 (dd, 1H), 7.85 (dd, 1H), 7.68 (d, 1H), 7.60 (dd, 1H), 7.50-7.44 (m, 1H), 7.40 (dd, 1H), 7.01-6.95 (m, 2H).

b) Synthesis of (1,3-pentanedionato-κO,κO')bis[2-(8-quinolinyl-κN)(3,5-difluorophenyl)-κC]iridium(III) (Ir3)

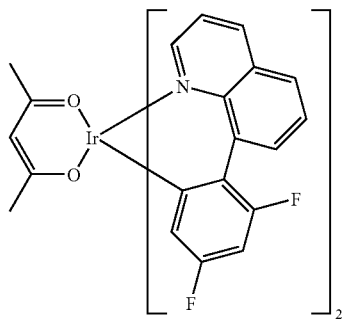

The procedure of Example 1 is repeated using 2.65 g (11.0 mmol) of 8-(2,4-difluorophenyl)quinoline instead of 8-phenylquinoline. The yield at a purity of 99.5% according to $^1$H-NMR is 1.78 g (2.3 mmol), corresponding to 46.1% of theory.

$^1$H-NMR (CDCl$_3$): δ [ppm]=8.45 (dd, 2H), 8.37 (dd, 2H), 8.14 (dd, 2H), 7.70-7.63 (m, 4H), 7.04 (dd, 2H), 6.50 (m, 2H), 6.11 (dd, 2H), 4.18 (s, 1H), 1.03 (s, 6H).

Example 4

(1,3-Pentanedionato-κO,κO')bis[2-(8-quinolinyl-κN)(4,6-difluoro-phenyl)-κC]iridium(III) (Ir4)

a) Synthesis of 8-(3,5-difluorophenyl)quinoline

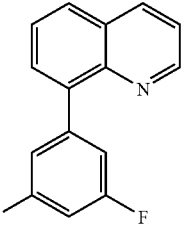

The procedure of Example 1 is repeated using 15.8 g (100 mmol) of 3,5-difluorobenzeneboronic acid instead of benzeneboronic acid. The yield at a purity of 99.5% according to $^1$H-NMR is 10.3 g (43 mmol), corresponding to 85.4% of theory.

$^1$H-NMR (CDCl$_3$): δ [ppm]=8.94 (dd, 1H), 8.18 (d, 1H), 7.84 (d, 1H), 7.69 (dd, 1H), 7.60 (dd, 1H), 7.42 (dd, 1H), 7.26-7.21 (m, 2H), 6.87 (m, 1H).

b) Synthesis of (1,3-pentanedionato-κO,κO')bis[2-(8-quinolinyl-κN)(4,6-difluorophenyl)-κC]iridium(III) (Ir4)

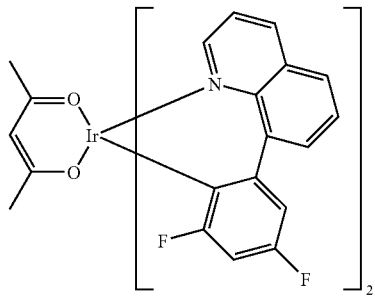

The procedure of Example 1 is repeated using 2.65 g (11.0 mmol) of 8-(3,5-difluorophenyl)quinoline instead of 8-phenylquinoline. The yield at a purity of 99.5% according to $^1$H-NMR is 2.24 g (2.9 mmol), corresponding to 58.0% of theory.

$^1$H-NMR (CDCl$_3$): δ [ppm]=8.55 (dd, 2H), 8.30 (dd, 2H), 8.09 (dd, 2H), 7.70-7.62 (m, 4H), 7.38 (dd, 2H), 6.99 (dd, 2H), 6.33 (m, 2H), 4.25 (s, 1H), 1.08 (s, 6H).

Example 5

Tris[5,7,7',9-tetramethyl-7H-indeno[2,1-h]quinolin-11-yl-κN,-κC]iridium(III) (Ir5)

a) Synthesis of 2,7,9,9-tetramethylfluorene

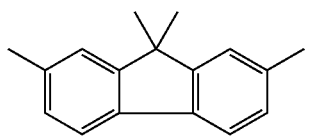

100 g (284 mmol) of 2,7-dibromo-9,9-dimethylfluorene are dissolved in 1000 ml of THF and, at −75° C., 227 ml (566 mmol) of n-butyllithium (2M in hexane) are added dropwise. After the addition, 53 ml (850 mmol) of methyl iodide are added dropwise at −78° C. The reaction mixture is allowed to warm to room temperature and is subsequently stirred for another 3 hours at room temperature. The reaction solution is subsequently admixed while cooling in ice with 120 ml of half concentrated hydrochloric acid and then with 400 ml of 50% strength ammonia solution. The resulting mixture is extracted with 300 ml of dichloromethane, the extract is dried over MgSO$_4$ and evaporated under reduced pressure. The solid obtained is filtered off with suction and washed with a little methanol. This gives 57.8 g (260 mmol) of a white solid, corresponding to 91.5% of theory, having a purity of 98.5%.

$^1$H-NMR (CDCl$_3$): δ [ppm]=7.56 (d, $^3J_{HH}$=7.7, 2H), 7.21 (s, 2H), 7.12 (d, $^3J_{HH}$=7.7 Hz, 2H), 2.41 (s, 6H), 1.45 (s, 6H).

b) Synthesis of 2,7,9,9-tetramethyl-4-nitrofluorene

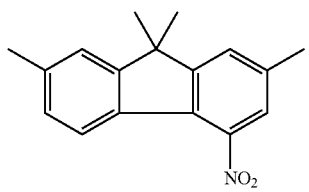

800 ml of dichloromethane are cooled to −75° C. and admixed with 26 ml (620 mmol) of nitric acid and 926 ml of acetic anhydride 114.3 g (513 mmol) of 2,7,9,9-tetramethylfluorene dissolved in 250 ml of dichloromethane are added quickly to this solution. The mixture is stirred at −75° C. for 5 hours and then slowly warmed to room temperature. The mixture is then evaporated under reduced pressure and purified by column chromatography using heptane:toluene (20:1). This gives 70.4 g (263 mmol) of a white solid, corresponding to 51.3% of theory, having a purity of 95.5%.

$^1$H-NMR (CDCl$_3$): δ [ppm]=7.91 (d, $^3J_{HH}$=8.3, 1H), 7.63 (s, 1H), 7.44 (s, 1H), 7.24 (s, 1H), 7.14 (d, $^3J_{HH}$=8.3 Hz, 1H), 2.47 (s, 3H), 2.43 (s, 3H), 1.47 (s, 6H).

c) Synthesis of 2,7,9,9-tetramethyl-4-aminofluorene

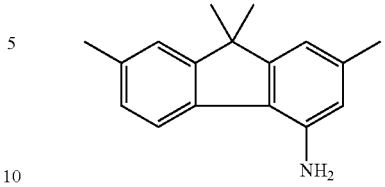

294 ml of concentrated hydrochloric acid, 1400 ml of ethanol and 67.5 g (253 mmol) of 2,7,9,9-tetramethyl-4-nitrofluorene are placed in a reaction vessel and 70.0 g (589 mmol) of tin powder are added a little at a time at room temperature. After the addition, the mixture is stirred at room temperature for 3 hours. The reaction mixture is then brought to a pH of 12 by addition of NaOH (solid) while cooling in ice. The residue is filtered, washed with dichloromethane and recrystallized from heptane. This gives 37.8 g (159 mmol) of a white solid, corresponding to 62.9% of theory, having a purity of 95.0%.

$^1$H-NMR (CDCl$_3$): δ [ppm]=7.65 (d, $^3J_{HH}$=7.7, 1H), 7.41 (s, 1H), 7.29 (d, $^3J_{HH}$=7.7 Hz, 1H), 6.89 (s, 1H), 6.58 (s, 1H), 4.15 (s, 2H), 2.59 (s, 3H), 2.49 (s, 3H), 1.62 (s, 6H).

d) Synthesis of 5,7,7,9-tetramethyl-7H-indeno[2,1-h]quinoline

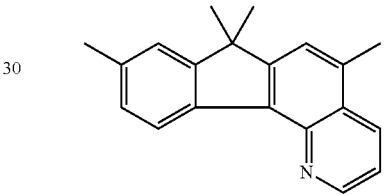

6.5 g (64 mmol) of concentrated sulphuric acid are added dropwise to a mixture of 4.9 g (20.6 mmol) of 2,7,9,9-tetramethyl-4-aminofluorene, 3.6 g (15.7 mmol) of arsenic(V) oxide and 7.16 g (77.3 mmol) of glycerol over a period of 15 minutes while stirring vigorously. The mixture is heated at 165° C. for 6 hours. After cooling to room temperature, it is poured into 70 ml of ice water, concentrated ammonia is added while cooling until the mixture has an alkaline reaction and the mixture is extracted with dichloromethane. After removal of the solvent, the residue is recrystallized from ethanol. This gives 1.4 g (5.1 mmol) of a yellow solid, corresponding to 24.7% of theory, having a purity of 99.7%.

$^1$H-NMR (CDCl$_3$): d [ppm]=9.03 (dd, $^4J_{HH}$=1.6 Hz, $^3J_{HH}$=4.0 Hz, 1H), 8.83 (d, $^3J_{HH}$=7.7 Hz, 1H), 8.36 (dd, $^4J_{HH}$=1.6 Hz, $^3J_{HH}$=8.3 Hz, 1H), 7.49 (s, 1H), 7.43 (dd, $^4J_{HH}$=4.0 Hz, $^3J_{HH}$=8.3 Hz, 1H), 7.29 (s, 1H), 7.24 (d, $^3J_{HH}$=7.7 Hz, 1H), 2.79 (s, 3H), 2.48 (s, 3H), 1.55 (s, 6H).

e) Synthesis of tris[5,7,7',9-tetramethyl-7H-indeno[2,1-h]quinolin-11-yl]iridium(III) (Ir5)

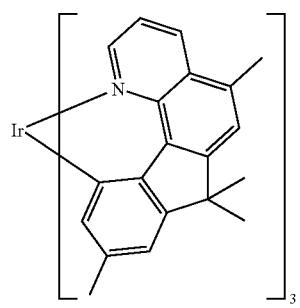

A mixture of 484 mg (1.0 mmol) of Na[Ir(acac)$_2$Cl$_2$], 1.64 g (6.0 mmol) of 5,7,7,9-tetramethyl-7H-indeno[2,1-h]quinoline and 10 ml of ethylene glycol is heated at 180° C. for 140 hours. After cooling, the mixture is poured into a mixture of 50 ml of ethanol and 25 ml of 1N hydrochloric acid and stirred at room temperature for 1 hour. The solid which has precipitated is filtered off with suction, washed three times with 30 ml of water and then three times with 30 ml of ethanol and dried under reduced pressure. The deep red solid is subsequently chromatographed on silica gel (CH$_2$Cl$_2$/n-hexane, 1:6). The yield is 332 mg (0.3 mmol), corresponding to 32.9% of theory, at a purity of 99.5% according to $^1$H-NMR.

$^1$H-NMR (CDCl$_3$): δ [ppm]=8.76 (d, 3H), 8.26 (d, 3H), 7.47 (s, 3H), 7.40 (dd, 3H), 7.01 (s, 3H), 6.83 (s, 3H), 3.02 (s, 9H), 2.67 (s, 9H), 1.63 (s, 18H).

Example 6

(1,3-Pentanedionato-κO,κO')[2-(8-quinolinyl-κN)phenyl-κC]platinum(II), (Pt1)

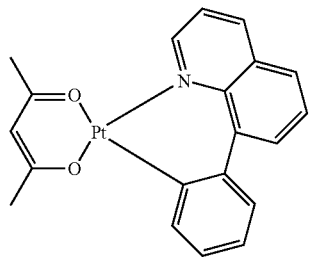

A mixture of 2.07 g (5.0 mmol) of potassium tetrachloroplatinate, 2.23 g (6.0 mmol) of 8-phenylquinoline, 75 ml of 2-ethoxyethanol and 25 ml of water is refluxed for 48 hours. The reaction mixture is evaporated under reduced pressure, the brown residue is taken up in a mixture of 200 ml of water and 100 ml of ethanol and stirred at 60° C. for 1 hour. The solid is filtered off with suction and washed three times with 100 ml of ethanol. The brown solid is then suspended in 50 ml of ethoxyethanol, admixed with 0.72 ml (7.0 mmol) of acetylacetone and 1.11 g (8.0 mmol) of potassium carbonate and refluxed for 16 hours. After cooling, the dark red precipitate is filtered off with suction, washed three times with 100 ml each time of a mixture of ethanol/water (1:1, v:v) and then three times with 100 ml of ethanol. After drying, the precipitate is dissolved in 200 ml of dichloromethane. The solution is filtered through silica gel and subsequently chromatographed on silica gel (CH$_2$Cl$_2$/n-hexane, 1:5). The yield is 0.81 g (1.6 mmol), corresponding to 32.4% of theory, at a purity of 99.5% according to $^1$H-NMR.

$^1$H-NMR (CDCl$_3$): δ [ppm]=8.63 (m, 1H), 8.31 (m, 1H), 8.08 (d, 1H), 7.67 (d, 1H), 7.68-7.64 (m, 2H), 7.01 (dd, 1H), 6.95 (d, 1H), 6.42-6.40 (m, 2H), 4.26 (s, 1H), 1.11 (br. s, 6H).

Example 7-13

Production and Characterization of Organic Electroluminescence Devices Comprising Compounds Ir1-Ir5 and Pt1 According to the Invention Electroluminescence devices according to the invention can be produced as described, for example, in WO 05/003253.

The results for two different OLEDs are compared here. The basic structure, the materials used, the degree of doping and their layer thicknesses are identical to allow better comparability. Only the dopant in the emission layer is varied.

The first example describes a comparative standard according to the prior art in which the emission layer comprises the host material CBP and the guest material Ir(piq)$_3$. In addition, an OLED having an emitter layer comprising the host material CBP and the guest materials Ir1 to Ir5 and Pt1 (prepared as described in Examples 1 to 6) is also described. OLEDs having the following structure are produced by a method analogous to the abovementioned general method:

PEDOT 60 nm (applied from water by spin coating; PEDOT procured from H. C. Starck, Goslar; poly[3,4-ethylenedioxy-2,5-thiophene]), (HIL)

NaphDATA 20 nm (applied by vapour deposition; NaphDATA procured from SynTec; 4,4',4"-tris(N-1-naphthyl)-N-phenylamino)triphenylamine, (HTL)

S-TAD 20 nm (applied by vapour deposition; S-TAD synthesized as described in WO 99/12888; 2,2',7,7'-tetrakis (diphenylamino)-spirobifluorene), (HTL)

Emitter layer: (EML)

CPB 20 nm (applied by vapour deposition; CPB procured from ALDRICH and purified further, finally sublimed twice more; 4,4'-bis(N-carbazolyl)biphenyl)

Ir1 to Ir5 or Pt1 (10% doping, applied by vapour deposition; synthesized as described in Example 1 to 6)

OR:

Ir(piq)$_3$ (10% doping, applied by vapour deposition, synthesized as described in WO 03/0068526), comparative example.

BCP 10 nm (applied by vapour deposition; BCP procured from ABCR, used as obtained; 2,9-dimethyl-4,7-diphenyl-1,10-phenanthroline), (HBL)

AlQ$_3$ 10 nm (applied by vapour deposition: AlQ$_3$ procured from SynTec; tris(quinolinato)aluminium(III)), (ETL)

LiF 1 nm

Al 100 nm

These not yet optimized OLEDs are characterized in a standard fashion; for this purpose, the electroluminescence spectra, the efficiency (measured in cd/A) as a function of the luminosity, calculated as current-voltage-luminosity curves (IUL curves), and the life are determined.

Efficiency as a Function of the Luminosity, Colour, Operating Voltage, Life:

OLEDs produced using the dopant Ir(piq)$_3$ typically give a maximum efficiency of about 6.5 cd/A at CIE colour coordinates of x=0.68, y=0.32 under the conditions described above. Voltages of 6.2 V are required for the reference luminance of 100 cd/m$^2$. The life is about 250 hours at an initial luminance of 500 cd/m$^2$ (cf. Table 1).

In contrast, OLEDs produced using the inventive dopants Ir1 to Ir5 display maximum efficiencies of from 4.8 to 6.8 cd/A at CIE colour coordinates of x=0.68-0.70, y=0.32-0.30, with the voltages required for the reference luminance of 100 cd/m$^2$ being in the range from 5.2 to 5.8 V (cf. Table 1). The life at an initial luminance of 500 cd/m$^2$ is from 280 hours to 470 hours and thus better than that of the reference material Ir(piq)$_3$ (cf. Table 1).

OLEDs produced using the inventive dopant Pt1 display a maximum efficiency of 4.3 cd/A at CIE colour coordinates of x=072, y=0.28, with the voltage required for the reference luminance of 100 cd/m$^2$ being 6.0 V (cf. Table 1). The life at an initial luminance of 500 cd/m$^2$ is 310 hours and thus better than that of the reference material Ir(piq)$_3$ (cf. Table 1).

TABLE 1

Device results using dopants according to the invention in CBP as matrix

| Experiment | EML | Max. efficiency [cd/A] | Voltage [V] at 100 cd/m$^2$ | CIE (x, y) | Life [h] at initial luminance of 500 [cd/m$^2$] |
|---|---|---|---|---|---|
| Example 7 (comparison) | CBP: 10% Ir(piq)$_3$ (30 nm) | 6.5 | 6.2 | 0.68/0.32 | 250 |
| Example 8 | CBP: 10% Ir1 (30 nm) | 4.8 | 5.2 | 0.70/0.30 | 390 |
| Example 9 | CBP: 10% Ir2 (30 nm) | 4.9 | 5.7 | 0.70/0.30 | 470 |
| Example 10 | CBP: 10% Ir3 (30 nm) | 6.8 | 5.8 | 0.68/0.32 | 420 |
| Example 11 | CBP: 10% Ir4 (30 nm) | 5.5 | 5.6 | 0.69/0.31 | 330 |
| Example 12 | CBP: 10% Ir5 (30 nm) | 6.6 | 5.3 | 0.68/0.32 | 370 |
| Example 13 | CBP: 10% Pt1 (30 nm) | 4.3 | 6.0 | 0.72/0.28 | 310 |

Examples 14 to 19

Further Device Examples Using Dopants According to the Invention

The inventive dopants Ir1 to Ir5 and Pt1 and also the comparative example Ir(piq)$_3$ according to the prior art are tested in OLEDs comprising the matrix material M1 as described in WO 04/093207. OLEDs having the following structure were produced by a method analogous to that of Examples 7-13:

PEDOT 80 nm (applied by spin coating from water; PEDOT procured from H. C. Starck, Goslar; poly[3,4-ethylene-dioxy-2,5-thiophene]), (HIL)

NaphDATA 20 nm (applied by vapour deposition; NaphDATA procured from SynTec; 4,4',4"-tris(N-1-naphthyl)-N-phenylamino)triphenyl-amine), (HTL)

S-TAD 20 nm (applied by vapour deposition; S-TAD synthesized as described in WO 99/12888; 2,2',7,7'-tetrakis(diphenylamino)spirobifluorene), (HTL)

Emitter layer: (EML)

M1 Bis(9,9'-spirobifluoren-2-yl)ketone (applied by vapour deposition, synthesized as described in WO 2004/093207)

Ir1 to Ir5 or Pt1 (10% doping, applied by vapour deposition; synthesized as in Examples 1 to 6)

OR:

Ir(piq)$_3$ (10% doping, applied by vapour deposition; synthesized as described in WO 03/0068526)

HBM1 2,7-Bis(4-biphenyl-1-yl)-2',7'-di-tert-butylspiro-9,9'-bifluorene (applied by vapour deposition; synthesized as described in WO 05/011334)

AlQ$_3$ (applied by vapour deposition; AlQ$_3$ procured from SynTec; tris(quinolinato)aluminium(III)), (ETL);

Ba—Al 3 nm of Ba, then 150 nm of Al on top of this.

These not yet optimized OLEDs are characterized in a standard fashion; for this purpose, the electroluminescence spectra, the efficiency (measured in cd/A) as a function of the luminosity, calculated as current-voltage-luminosity curves (IUL curves), and the life are determined. The results obtained using these OLEDs are summarized in Table 2.

The matrix material M1, the hole blocking material HBM1 and the comparative dopant Ir(piq)$_3$ are shown below in the interests of clarity:

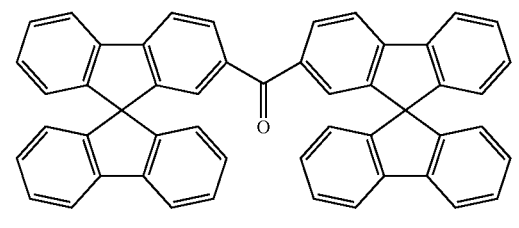

bis(9,9'-spirobifluoren-2-yl) ketone, matrix material M1

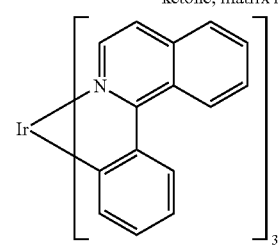

Ir(piq)$_3$

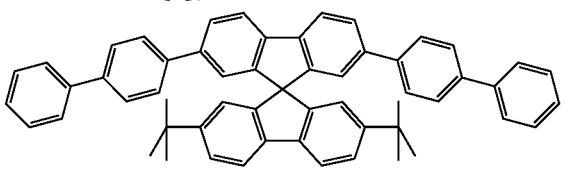

2,7-bis(4-phenyl-1-yl)-2',7'-di-tert-butylspiro-9,9'-bifluorene HBM1

TABLE 2

Device results using dopants according to the invention in M1 as matrix

| Experiment | EML | Max. efficiency [cd/A] | Voltage [V] at 100 cd/m$^2$ | CIE (x, y) | Life [h] at initial luminance of 1000 [cd/m$^2$] |
|---|---|---|---|---|---|
| Example 7 (comparative) | M1: 10% Ir(piq)$_3$ (30 nm) | 7.4 | 5.8 | 0.68/0.32 | 8300 |

TABLE 2-continued

Device results using dopants according to the invention in M1 as matrix

| Experiment | EML | Max. efficiency [cd/A] | Voltage [V] at 100 cd/m² | CIE (x, y) | Life [h] at initial luminance of 1000 [cd/m²] |
|---|---|---|---|---|---|
| Example 14 | CBP: 10% Ir1 (30 nm) | 5.3 | 5.0 | 0.70/0.30 | 16500 |
| Example 15 | M1: 10% Ir2 (30 nm) | 5.5 | 4.9 | 0.70/0.30 | 13600 |
| Example 16 | M1: 10% Ir3 (30 nm) | 8.2 | 5.3 | 0.68/032 | 15100 |
| Example 17 | M1: 10% Ir4 (30 nm) | 7.7 | 5.2 | 0.69/0.31 | 9700 |
| Example 18 | M1: 10% Ir5 (30 nm) | 8.7 | 5.1 | 0.68/0.32 | 17500 |
| Example 19 | M1: 10% Pt1 (30 nm) | 4.8 | 4.9 | 0.71/0.29 | 14200 |

The invention claimed is:

1. A compound of the formula (1)

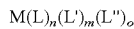
$$M(L)_n(L')_m(L'')_o \qquad \text{Formula (1)}$$

wherein substructure $M(L)_n$ of formula (1) is of the formula (2)

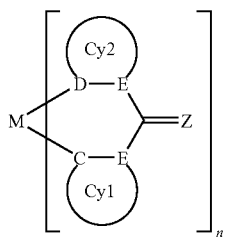

Formula (2)

wherein

M is a transition metal;

D identically or differently on each occurrence is an sp²-hybridized heteroatom having a nonbonding electron pair coordinated to M;

C is an sp²-hybridized carbon atom bound to M;

E identically or differently on each occurrence is an sp²-hybridized carbon or nitrogen atom;

Z identically or differently on each occurrence is $C(R)_2$ or NR;

Cy1 identically or differently on each occurrence is a homocycle or heterocycle bound to M via an sp²-hybridized carbon atom and is optionally bonded to R;

Cy2 identically or differently on each occurrence is a heterocycle coordinated to M via D and is optionally bonded to R;

R identically or differently on each occurrence is H; F; CN; a straight-chain alkyl or straight-chain alkoxy group having up to 40 carbon atoms; or a branched or cyclic alkyl or branched or cyclic alkoxy group having from 3 to 40 carbon atoms;

wherein one or more nonadjacent $CH_2$ groups in said straight-chain alkyl, straight-chain alkoxy, branched or cyclic alkyl, or branched or cyclic alkoxy groups is optionally replaced by $-R^2C=CR^2-$, $-C\equiv C-$, $Si(R^2)_2$, $Ge(R^2)_2$, $Sn(R^2)_2$, $-O-$, $-S-$, $-NR^2-$, $-(C=O)-$, $-(C=NR^2)-$, $-P=O(R^2)-$, SO, $SO_2$, or $-CONR^2-$; and wherein one or more H atoms is optionally replaced by F, an aromatic or heteroaromatic ring system having from 5 to 40 aromatic ring atoms, or an aryloxy or heteroaryloxy group having from 5 to 40 aromatic ring atoms, wherein said aromatic or heteroaromatic ring system, or aryloxy or heteroaryloxy group is optionally substituted by one or more nonaromatic radicals R; or a combination of two, three or four of these systems; and wherein R together with Cy1 and/or Cy2 optionally define an aliphatic, aromatic, or heteroaromatic ring system;

$R^2$ identically or differently on each occurrence is H or an aliphatic or aromatic hydrocarbon radical having up to 20 carbon atoms;

n is 1, 2 or 3; and wherein

L' and L'' are monoanionic, bidentate chelating ligands;

m and o identically or differently on each occurrence are 0, 1 or 2; and the sum of n, m, and o is 2 or 3.

2. The compound according to claim 1, wherein Cy1 and Cy2 are aromatic or heteroaromatic systems.

3. The compound according to claim 2, wherein substructure $M(L)_n$ is of the formula (2a)

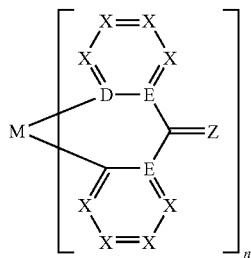

Formula (2a)

wherein

M on each occurrence is Mo, W, Re, Ru, Os, Rh, Ir, Pd, Pt, or Au;

D identically or differently on each occurrence is nitrogen or phosphorus;

X identically or differently on each occurrence is $CR^1$, N, or P;

(X—X) or (X=X) is $NR^1$, S, or O, with the proviso that Cy1 and Cy2 are each a five- or six-membered ring; or is $CR^1$, N, or P, if E in the corresponding ring is N;

E identically or differently on each occurrence is C or N, with the proviso that, if E is N, only one (X—X) in the corresponding ring is $CR^1$, N or P;

R identically or differently on each occurrence is H; F; CN; a straight-chain alkyl or straight-chain alkoxy group having up to 40 carbon atoms; or a branched or cyclic alkyl or branched or cyclic alkoxy group having from 3 to 40 carbon atoms;

wherein one or more nonadjacent $CH_2$ groups in said straight-chain alkyl, straight-chain alkoxy, branched or cyclic alkyl, or branched or cyclic alkoxy groups is optionally replaced by $-R^2C=CR^2-$, $-C\equiv C-$, $Si(R^2)_2$, $Ge(R^2)_2$, $Sn(R^2)_2$, $-O-$, $-S-$, $-NR^2-$, $-(C=O)-$, $-(C=NR^2)-$, $-P=O(R^2)-$, $SO$, $SO_2$, or $-CONR^2-$; and wherein one or more H atoms is optionally replaced by F, an aromatic or heteroaromatic ring system having from 5 to 40 aromatic ring atoms, or an aryloxy or heteroaryloxy group having from 5 to 40 aromatic ring atoms, wherein said aromatic or heteroaromatic ring system, or aryloxy or heteroaryloxy group is optionally substituted by one or more nonaromatic radicals R; or a combination of two, three or four of these systems; wherein R together with Cy1 and/or Cy2 optionally defines an aliphatic, aromatic, or heteroaromatic ring system; and wherein R together with X or $R^1$ optionally defines a ring system;

$R^1$ identically or differently on each occurrence is H; F; Cl; Br; I; OH; $NO_2$; CN;

$N(R^2)_2$; a straight-chain alkyl, straight-chain alkoxy, or straight-chain thioalkoxy group having up to 40 carbon atoms; or a branched or cyclic alkyl, branched or cyclic alkoxy, or branched or cyclic thioalkoxy group having from 3 to 40 carbon atoms; wherein one or more nonadjacent $CH_2$ groups of said straight-chain alkyl, straight-chain alkoxy, straight-chain thioalkoxy, branched or cyclic alkyl, branched or cyclic alkoxy, or branched or cyclic thioalkoxy group is optionally replaced by $-R^2C=CR^2-$, $-C\equiv C-$, $Si(R^2)_2$, $Ge(R^2)_2$, $Sn(R^2)_2$, $-O-$, $-S-$, $-NR^2-$, $-(C=O)-$, $-(C=NR^1)-$, $-P=O(R^2)-$, $SO$, $SO_2$, $-COOR^2-$, or $-CONR^2-$; and wherein one or more H atoms is optionally replaced by F; Cl; Br; I; CN; an aromatic or heteroaromatic ring system having from 5 to 40 aromatic ring atoms; or an aryloxy or heteroaryloxy group having from 5 to 40 aromatic ring atoms, and wherein said aromatic or heteroaromatic ring system or aryloxy or heteroaryloxy group is optionally substituted by one or more nonaromatic radicals $R^1$; or a combination of two, three or four of these systems; and wherein a plurality of $R^1$, either on the same ring or on different rings, or $R^1$ and R and/or $R^2$ optionally define a monocyclic or polycyclic, aliphatic, aromatic or heteroaromatic ring system.

4. The compound according to claim 3, wherein at least one substructure $M(L)_n$ identically or differently on each occurrence is of the formula (2b)

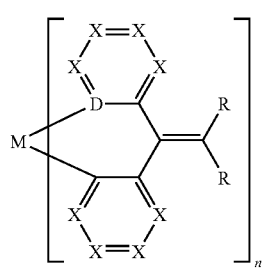

Formula (2b)

and wherein said compound optionally further comprises, identically or differently on each occurrence, a substructure $M(L')_m$ of the formula (3)

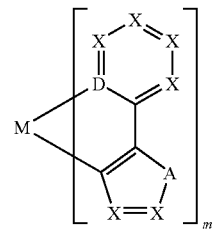

Formula (3)

wherein

X identically or differently on each occurrence is $CR^1$, N or P; or (X—X) or (X=X) are $NR^1$, S or O;

A identically or differently on each occurrence is $-CR^1=CR^1-$, $-N=CR^1-$, $-P=CR^1-$, $-N=N-$, $-P=N-$, $NR^1$, $PR^1$, O, S, or Se.

5. The compound according to claim 1, wherein substructure $M(L)_n$, is of the formula (2c), of the formula (2d) or of the formula (2e)

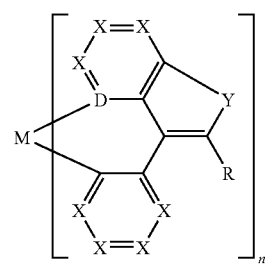

Formula (2c)

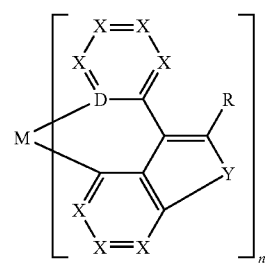

Formula (2d)

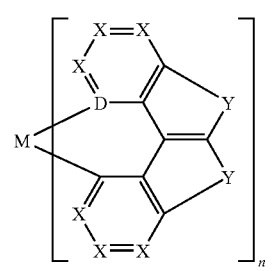

Formula (2e)

wherein Y, identically or differently on each occurrence, is a bivalent group selected from the group consisting of $-C(R^1)_2-$, $-C(=O)-$, $-C[=C(R^1)_2]-$, $-C(R^1)_2-C(R^1)_2-$, $-C(=O)-O-$, $-C(=O)-N(R^1)-$, $-C(R^1)_2-C(R^1)_2-C(R^1)_2-$, $-C(R^1)_2-$ O—C(R$^1$)$_2$—, —C(R$^1$)$_2$—N(R$^1$)—, —C(R$^1$)=C(R$^1$)—, —C(R$^1$)=N—, —O—, —S—, —N(R$^1$)—, —P(R$^1$)—, P(=O)(R$^1$)—, and —B(R$^1$)—.

6. The compound according to claim 1, wherein L″ is selected from the group consisting of 1,3-diketonates derived from 1,3-diketones, 3-ketonates derived from 3-keto esters, carboxylates derived from aminocarboxylic acids, salicyliminates derived from salicylimines, and borates of nitrogen-containing heterocycles.

7. The compound according to claim 1, wherein M is Rh, Ir, Pd, or Pt.

8. The compound according to claim 1, wherein n is 2 or 3.

9. The compound according to claim 1, wherein o is 0.

10. The compound according to claim 1, wherein Z is C(R)$_2$.

11. The compound according to claim 1, wherein D is N.

12. The compound according to claim 3, wherein X is CR$^1$ or N.

13. The compound according to claim 5, wherein Y is —C(R$^1$)$_2$—, —C(=O)—, —C(R$^1$)$_2$—C(R$^1$)$_2$—, —C(R$^1$)$_2$—N(R$^1$)—, —C(R$^1$)=C(R$^1$)—, —C(R$^1$)=N—, —O—, —S—, or —N(R$^1$)—.

14. The compound according to claim 1, wherein said compound is selected from the group consisting of structures (1) to (141)

(1)
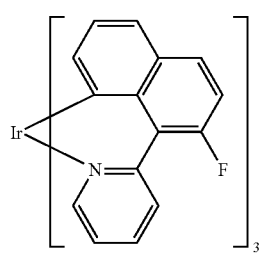

(2)
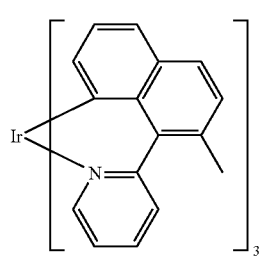

(3)
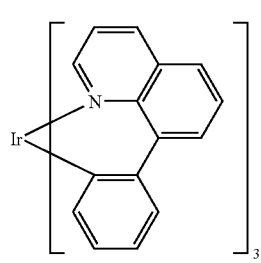

(4)
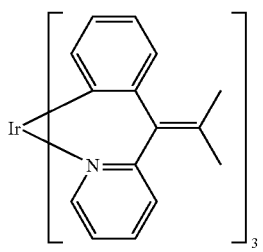

(5)
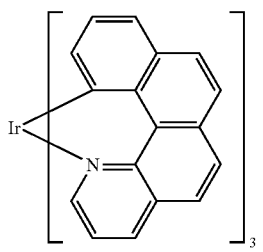

(6)
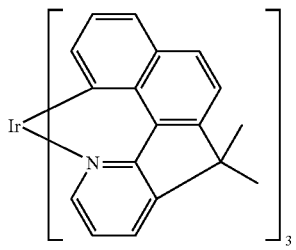

(7)
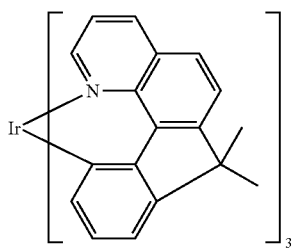

(8)
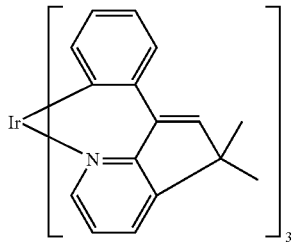

(9)
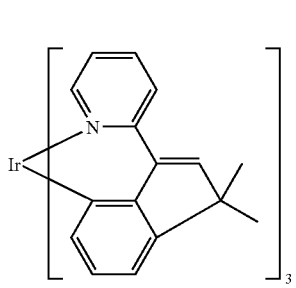

-continued
(10) 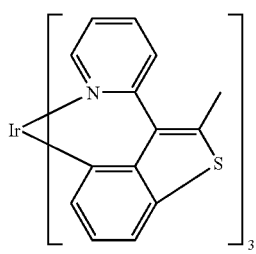
(11) 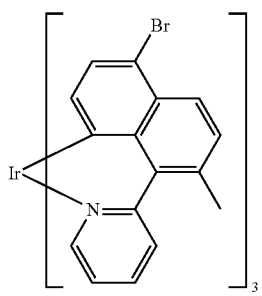
(12) 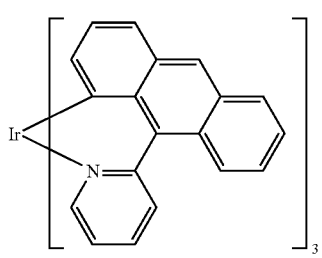
(13) 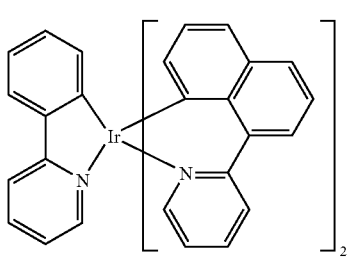
(14) 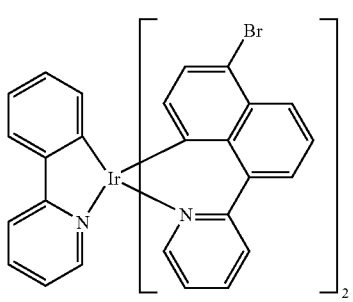
(15) 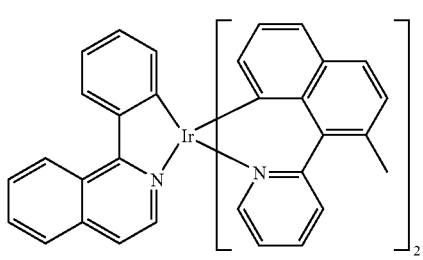
-continued
(16) 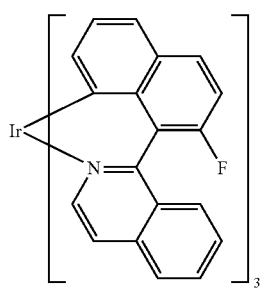
(17) 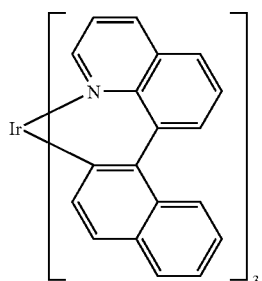
(18) 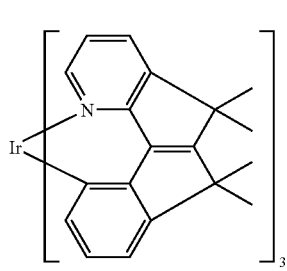
(19) 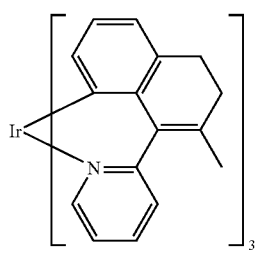
(20) 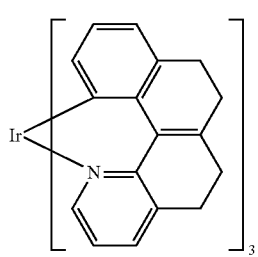
(21) 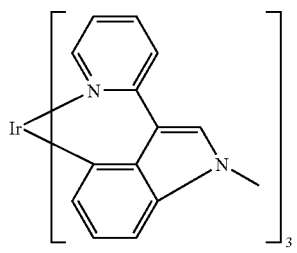

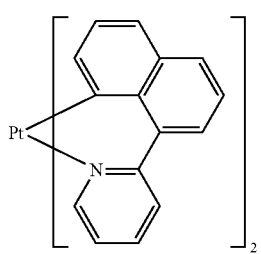 (22)
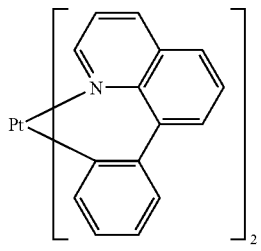 (23)
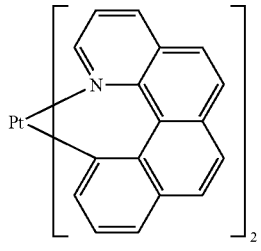 (24)
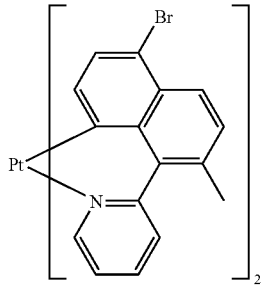 (25)
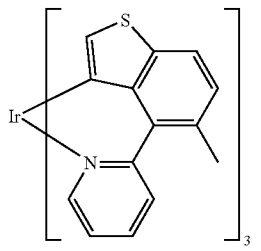 (26)
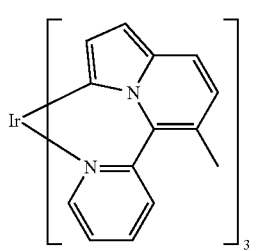 (27)
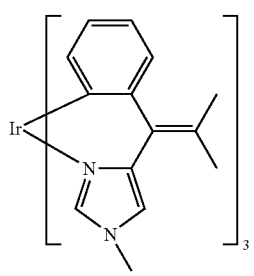 (28)
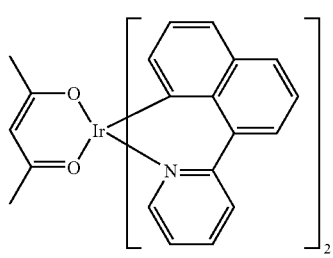 (29)
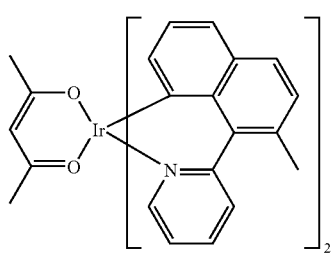 (30)
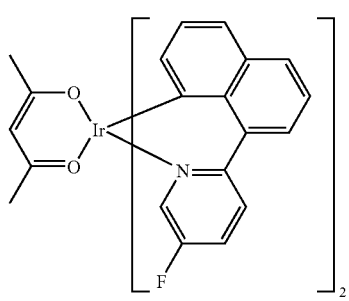 (31)
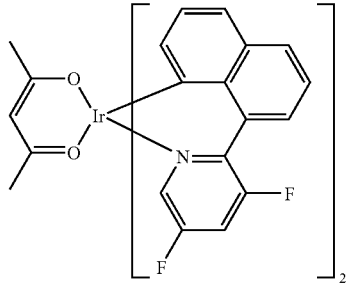 (32)

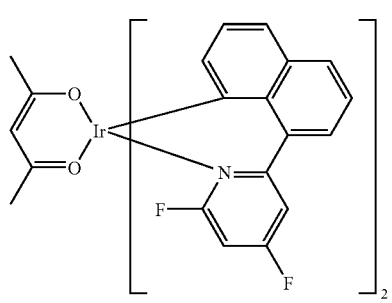
(33)
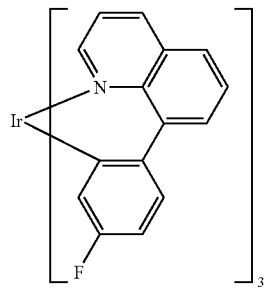
(34)
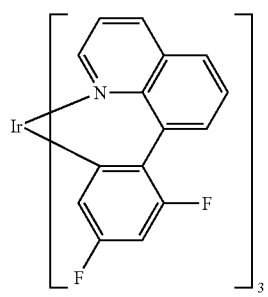
(35)
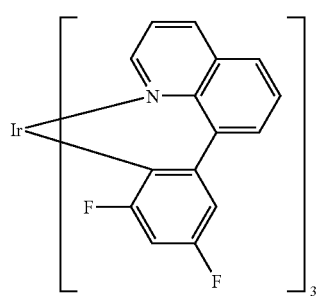
(36)
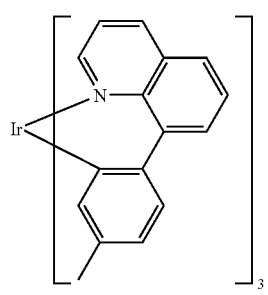
(37)
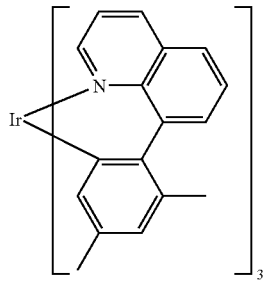
(38)
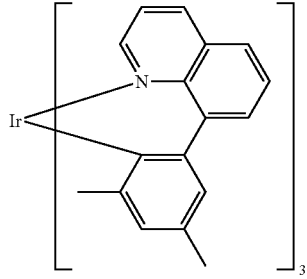
(39)
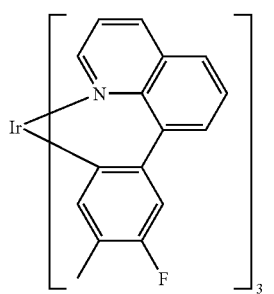
(40)
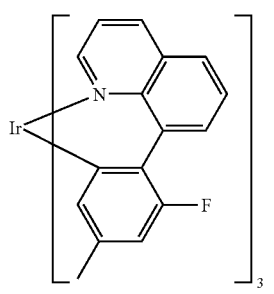
(41)
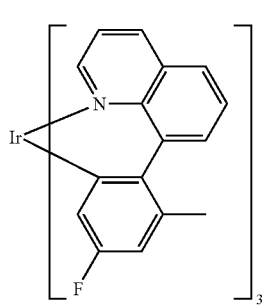
(42)

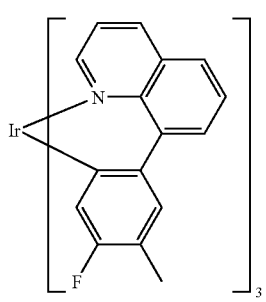 (43)
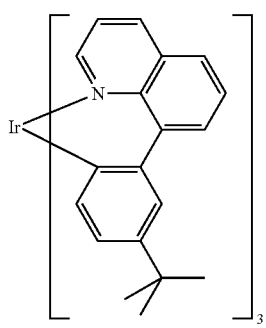 (44)
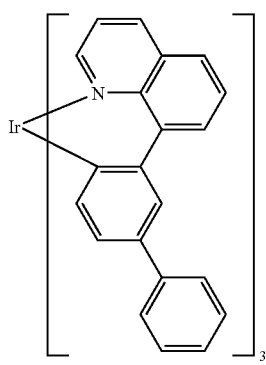 (45)
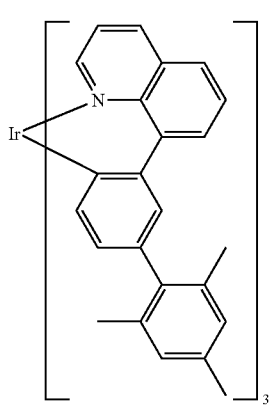 (46)
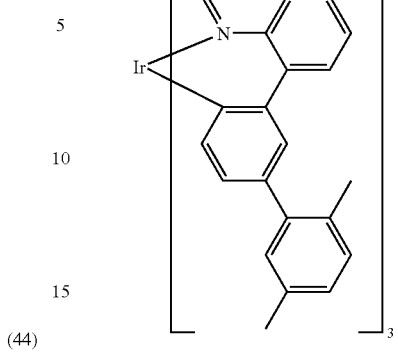 (46)
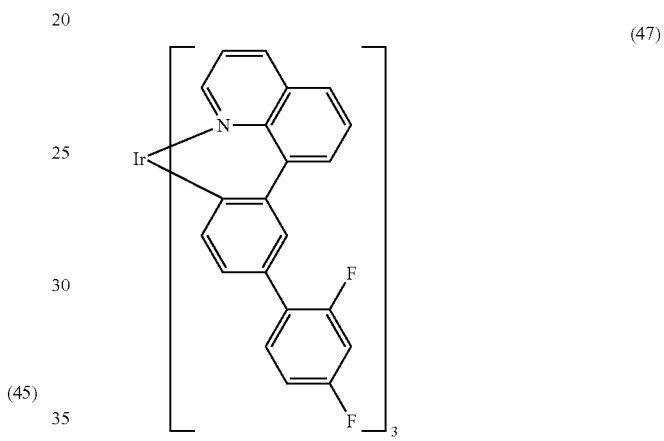 (47)
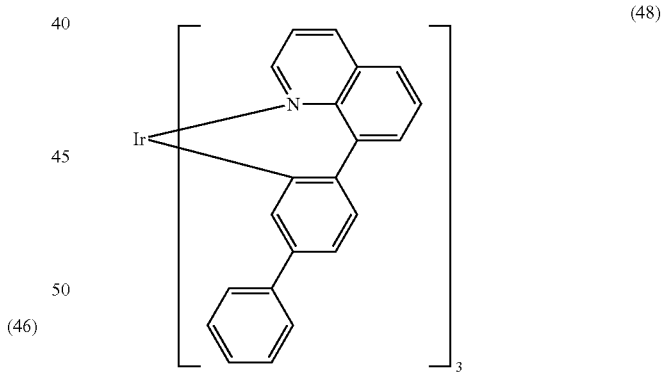 (48)
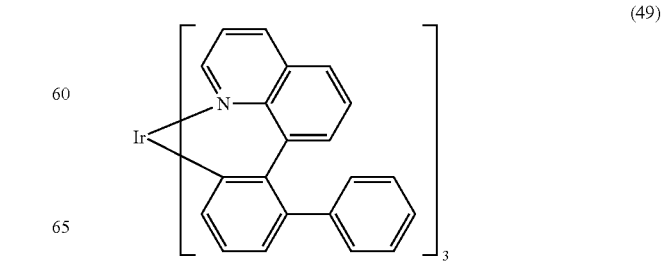 (49)

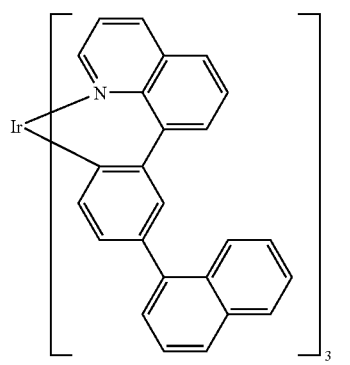 (50)
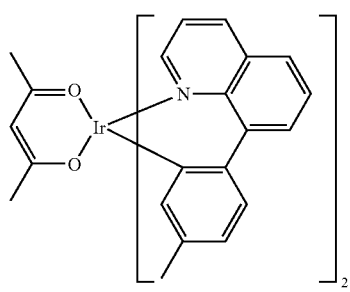 (51)
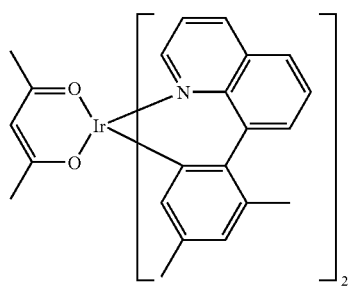 (52)
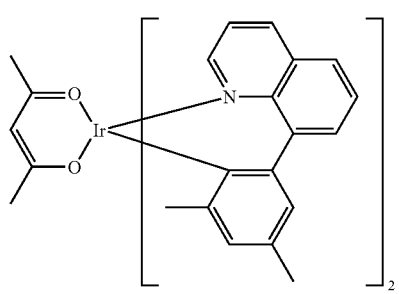 (53)
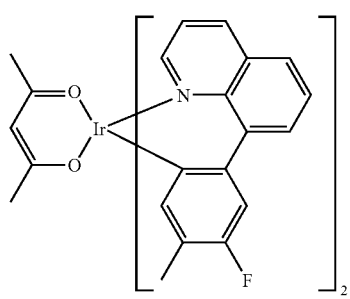 (54)
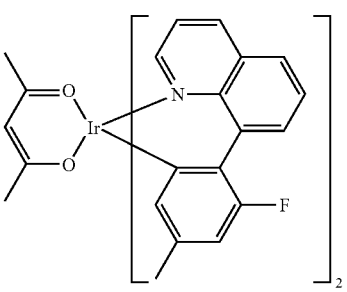 (55)
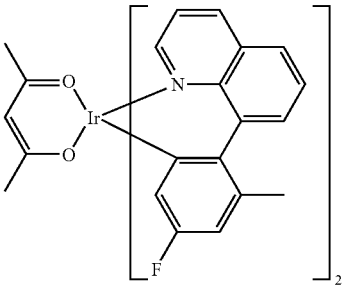 (56)
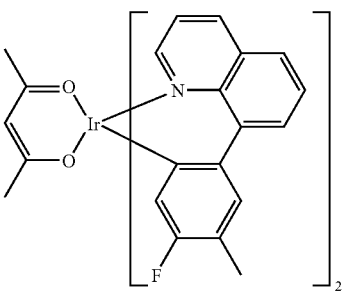 (57)
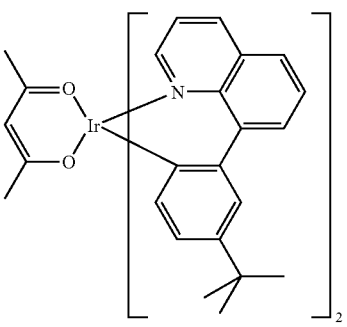 (58)
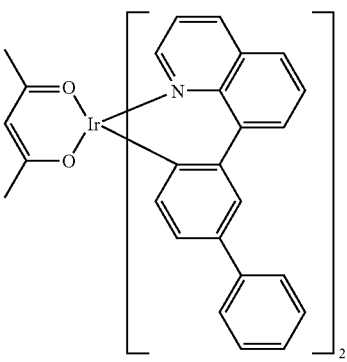 (59)

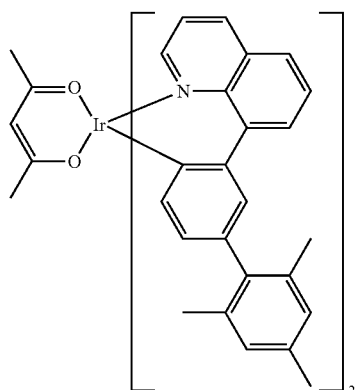
(60)
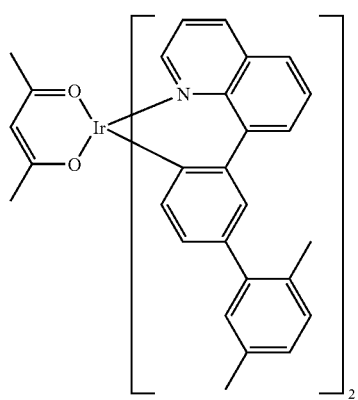
(61)
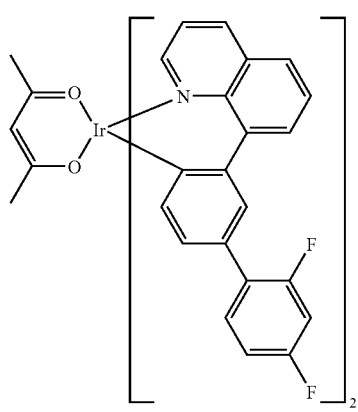
(62)
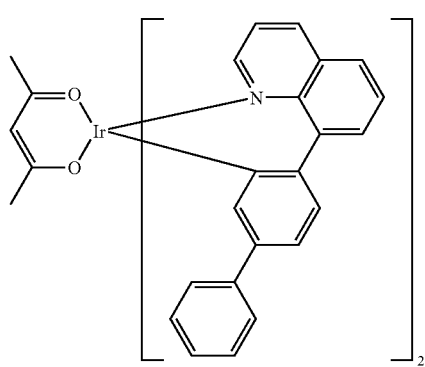
(64)
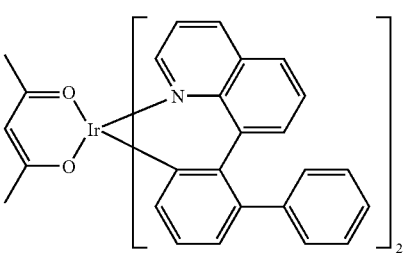
(65)
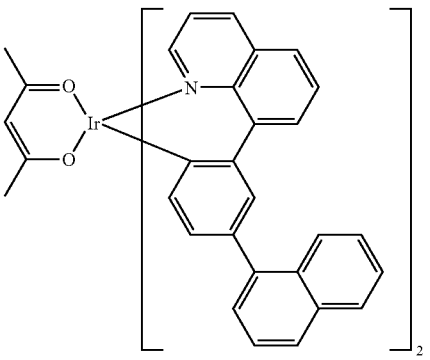
(66)
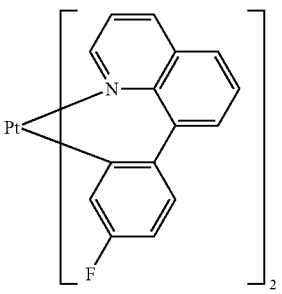
(67)
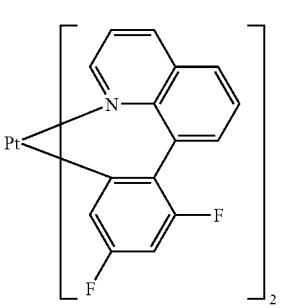
(68)
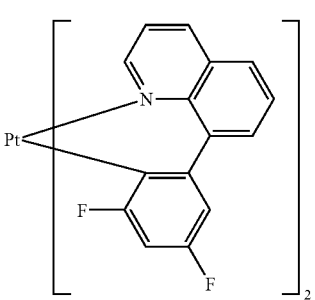
(69)

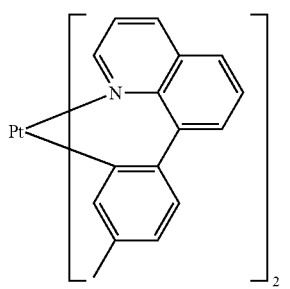
(70)
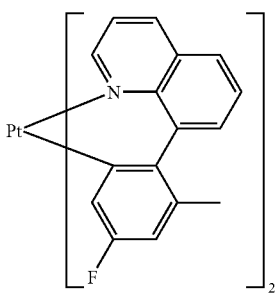
(75)
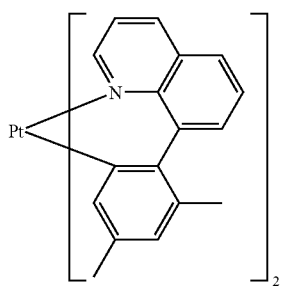
(71)
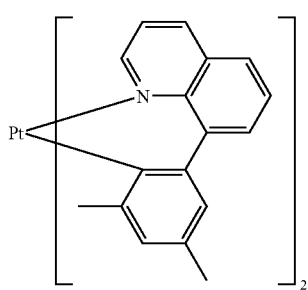
(72)
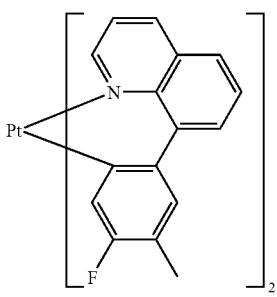
(76)
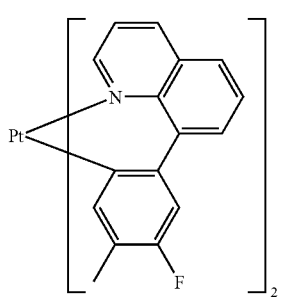
(73)
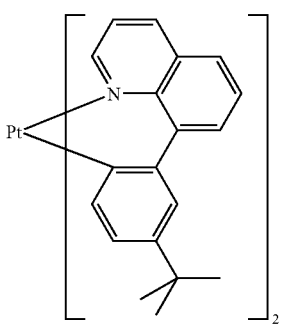
(77)
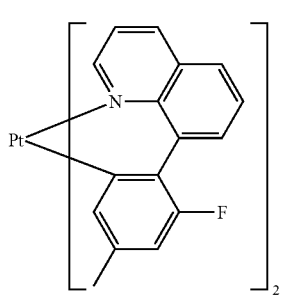
(74)
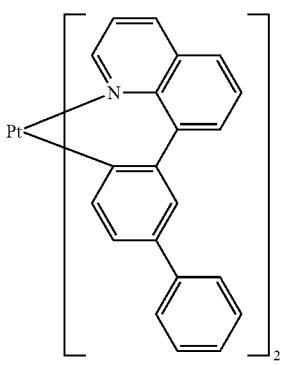
(78)

(79) 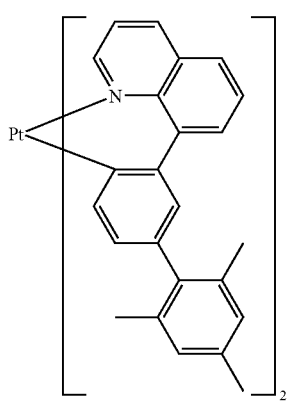
(80) 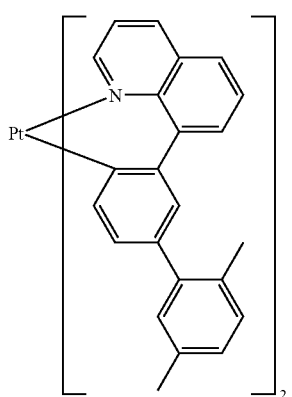
(81) 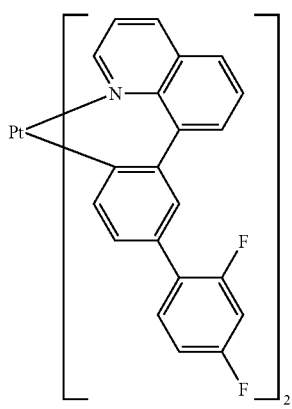
(82) 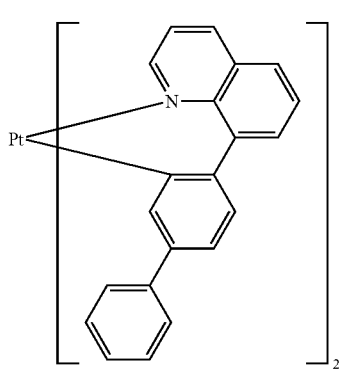
(83) 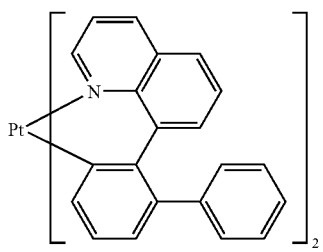
(84) 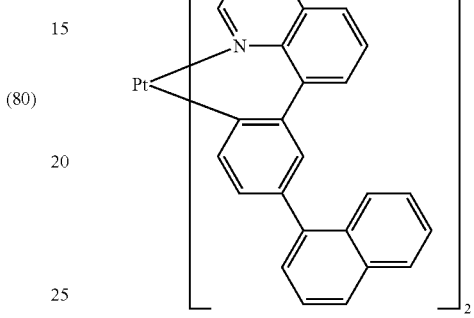
(85) 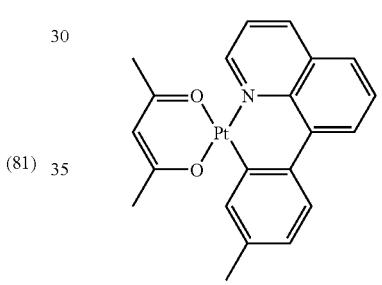
(86) 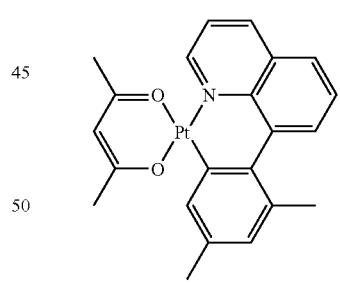
(87) 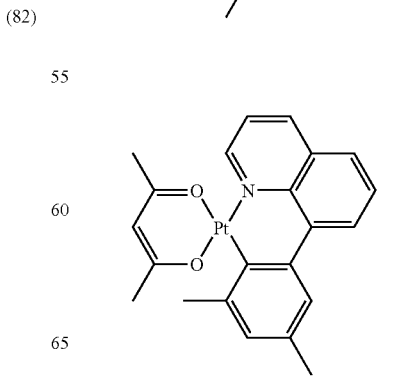

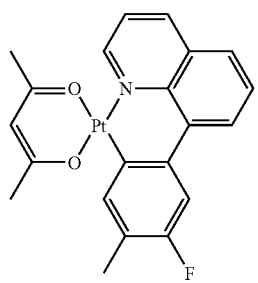 (88)
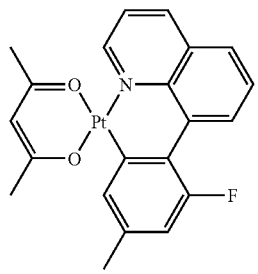 (89)
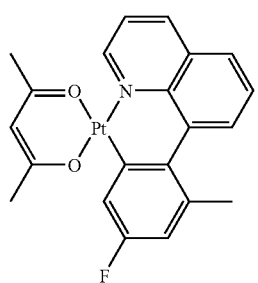 (90)
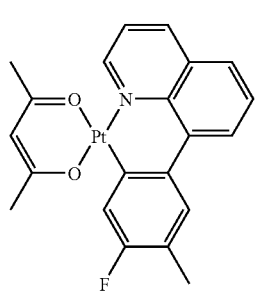 (91)
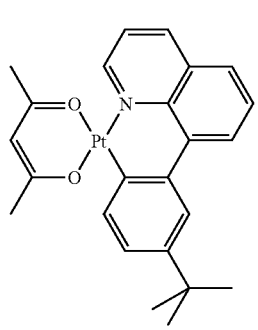 (92)
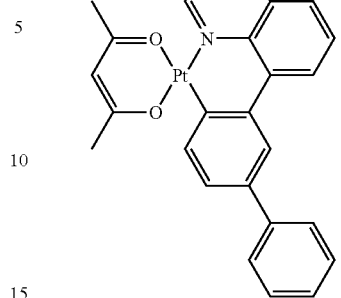 (93)
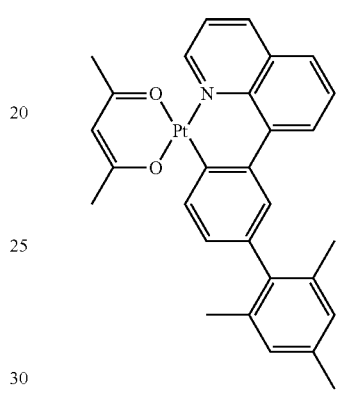 (94)
 (95)
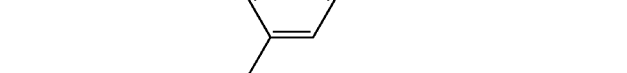
 (96)

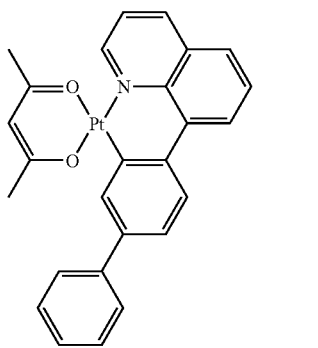
(97)
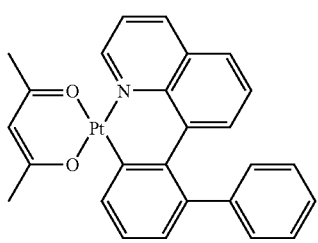
(98)
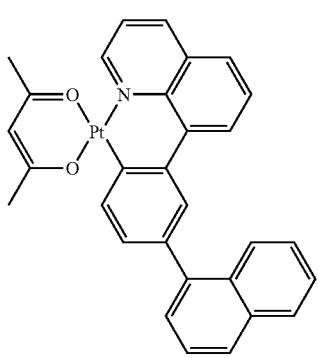
(99)
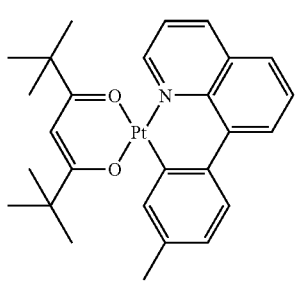
(100)
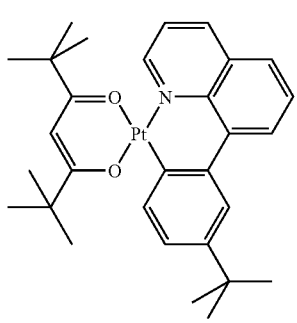
(101)
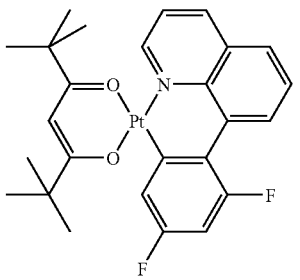
(102)
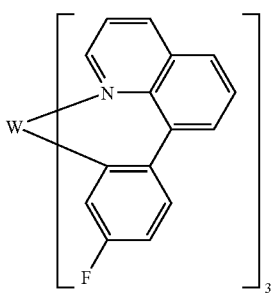
(103)
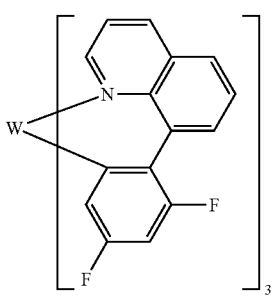
(104)
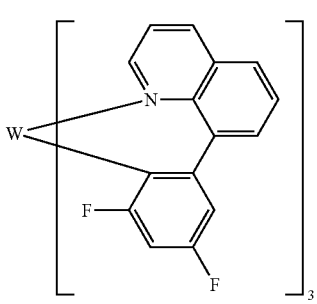
(105)
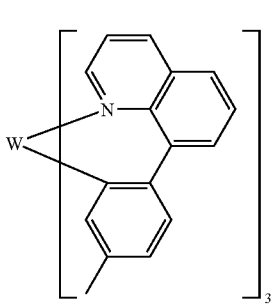
(106)

-continued
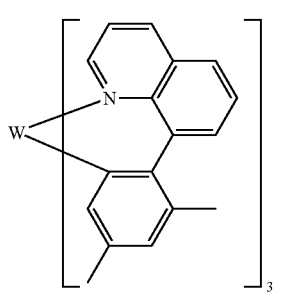
(107)
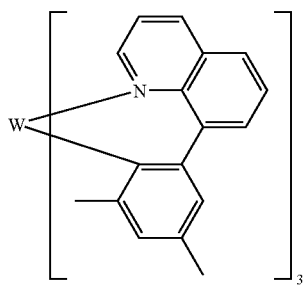
(108)
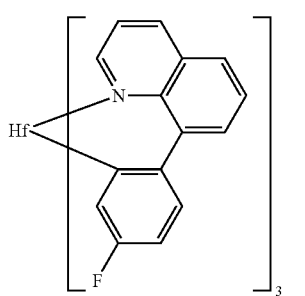
(109)
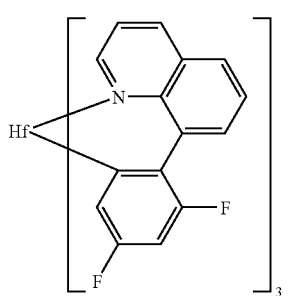
(110)
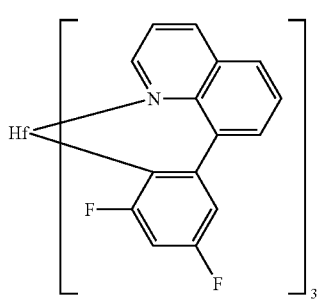
(111)
-continued
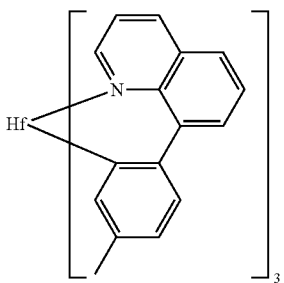
(112)
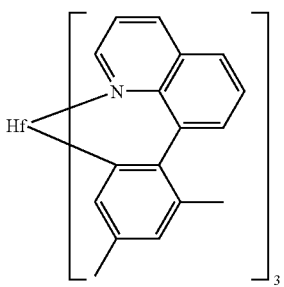
(113)
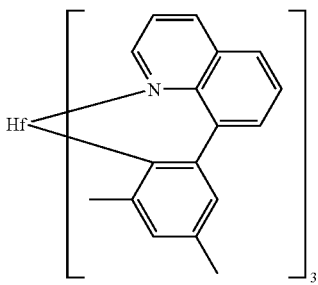
(114)
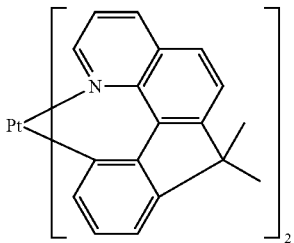
(115)
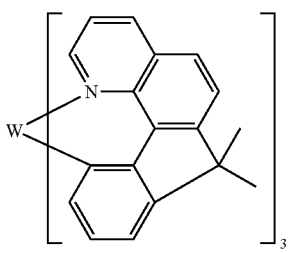
(116)
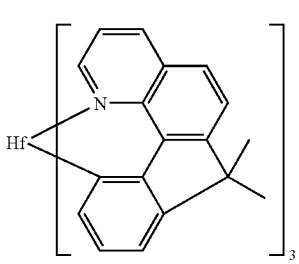
(117)

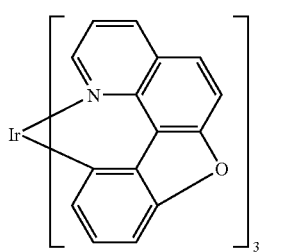
(118)
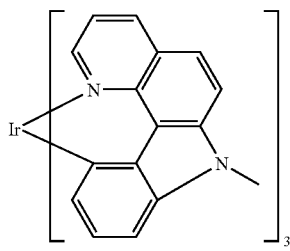
(119)
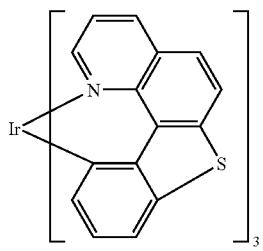
(120)
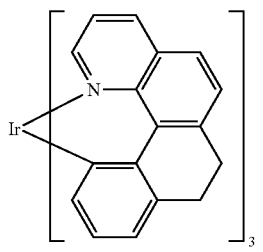
(121)
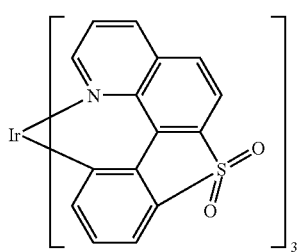
(122)
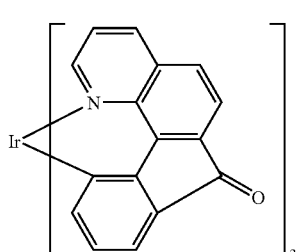
(123)
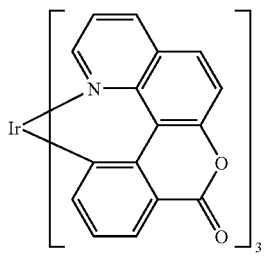
(124)
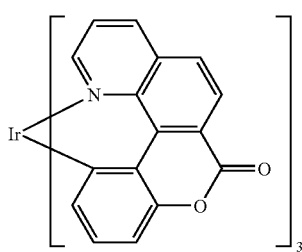
(125)
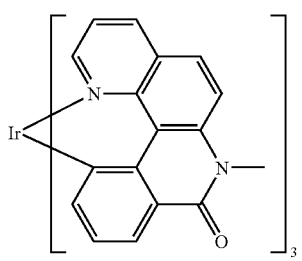
(126)
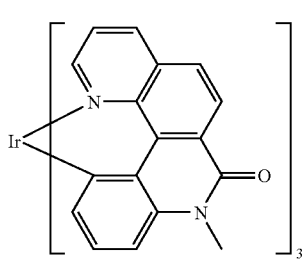
(127)
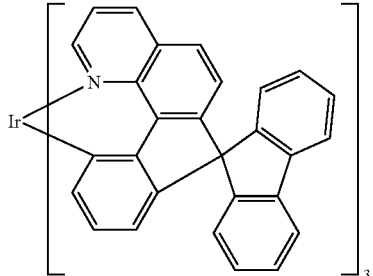
(128)
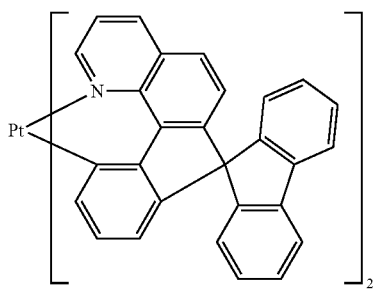
(129)

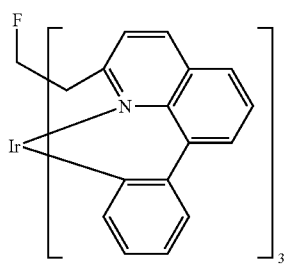(130)
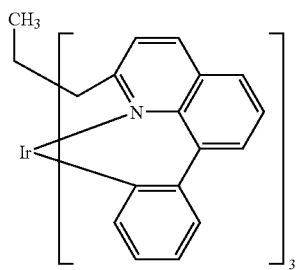(131)
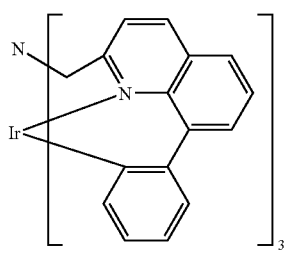(132)
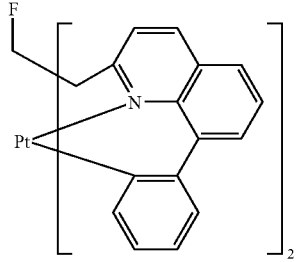(133)
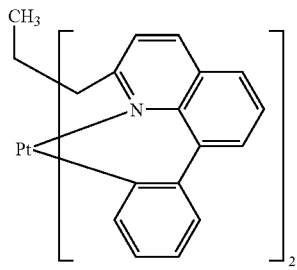(134)
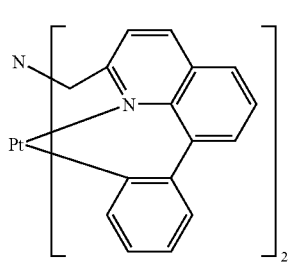(135)
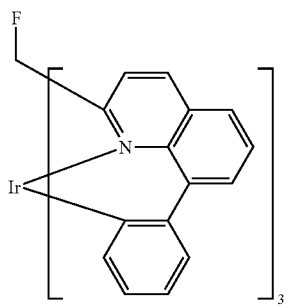(136)
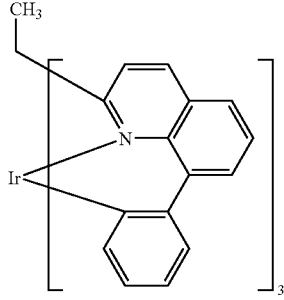(137)
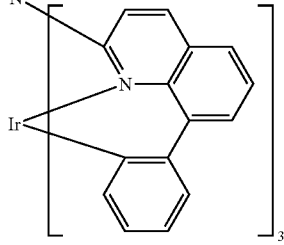(138)
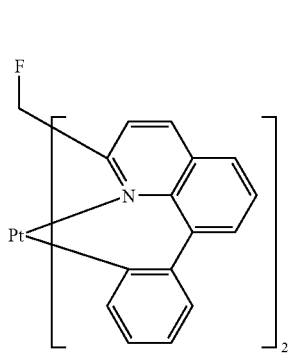(139)
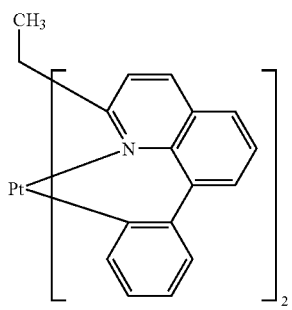(140)

-continued (141)

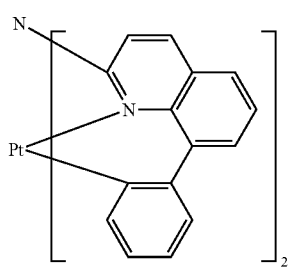

and wherein said compound is optionally substitued by $R^1$, wherein $R^1$ identically or differently on each occurrence is H; F; Cl; Br; I; OH; $NO_2$; CN; $N(R^2)_2$; a straight-chain alkyl, straight-chain alkoxy, or straight-chain thioalkoxy group having up to 40 carbon atoms; or a branched or cyclic alkyl, branched or cyclic alkoxy, or branched or cyclic thioalkoxy group having from 3 to 40 carbon atoms; wherein one or more nonadjacent $CH_2$ groups of said straight-chain alkyl, straight-chain alkoxy, straight-chain thioalkoxy, branched or cyclic alkyl, branched or cyclic alkoxy, or branched or cyclic thioalkoxy group is optionally replaced by —$R^2C$=$CR^2$—, —C≡C—, $Si(R^2)_2$, $Ge(R^2)_2$, $Sn(R^2)_2$, —O—, —S—, —$NR^2$—, —(C=O)—, —(C=$NR^1$)—, —P=$O(R^2)$—, SO, $SO_2$, —$COOR^2$—, or —$CONR^2$—; and wherein one or more H atoms is optionally replaced by F; Cl; Br; I; CN; an aromatic or heteroaromatic ring system having from 5 to 40 aromatic ring atoms; or an aryloxy or heteroaryloxy group having from 5 to 40 aromatic ring atoms, and wherein said aromatic or heteroaromatic ring system or aryloxy or heteroaryloxy group is optionally substituted by one or more nonaromatic radicals $R^1$; or a combination of two, three or four of these systems; and wherein a plurality of $R^1$, either on the same ring or on different rings, or $R^1$ and R and/or $R^2$ optionally define a monocyclic or polycyclic, aliphatic, aromatic or heteroaromatic ring system.

15. A process for preparing compounds according to claim 1 comprising the step of reacting the corresponding free ligands with metal alkoxides of formula (4), metal ketoketonates of formula (5), or mononuclear or multinuclear metal halides of formulae (6), (7), or (8)

$M(OR^2)_3$     Formula (4)

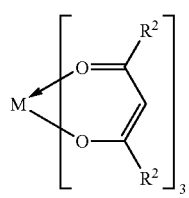 Formula (5)

$MHal_3$     Formula (6)

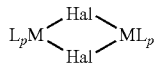 Formula (7)

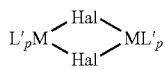 Formula (8)

wherein

M and $R^2$ are as defined in claim 1, p is 1 or 2; and

Hal is F, Cl, Br, or I.

16. A process for preparing compounds according to claim 1 comprising the step of reacting the corresponding free ligands with metal compounds which bear both alkoxide and/or halide and/or hydroxy and also ketoketonate radicals.

17. A conjugated, partly conjugated, or nonconjugated oligomer, polymer, or dendrimer comprising one or more compounds according to claim 1, wherein at least one of R or $R^1$ is a bond to said oligomer, polymer, or dendrimer.

18. The oligomer, polymer, or dendrimer according to claim 17, wherein said oligomer, polymer, or dendrimer is selected from the group consisting of polyfluorenes, polyspirobifluorenes, poly-para-phenylenes, polydihydrophenanthrenes, polyphenanthrenes, polyindenofluorenes, polycarbazoles, polyketones, polysilanes, polythiophenes, and copolymers thereof.

19. The oligomer, polymer, or dendrimer according to claim 17, wherein said one or more compounds according to claim 1 is incorporated into the side chain or into the main chain of said oligomer, polymer, or dendrimer or represent branching points of the polymer chains or end groups of the polymer chains.

20. An electronic component comprising one or more compounds according to claim 1.

21. An electronic component comprising one or more oligomers, polymers, or dendrimers according to claim 17.

22. The electronic components according to claim 21 selected from the group consisting of organic light-emitting diodes, polymeric light-emitting diodes, organic field effect transistors, organic thin film transistors, organic integrated circuits, organic solar cells, organic light-emitting transistors, organic field quench devices, light-emitting electrochemical cells, and organic laser diodes.

* * * * *